US009827303B2

(12) United States Patent
Kraan et al.

(10) Patent No.: US 9,827,303 B2
(45) Date of Patent: Nov. 28, 2017

(54) METHODS AND COMPOSITIONS FOR STABILIZING DRIED BIOLOGICAL MATERIALS

(71) Applicant: De Staat der Nederlanden, vert. door de minister van VWS, Ministerie van Volksgezondheid, Welzijn en Sport, The Hague (NL)

(72) Inventors: Heleen Kraan, Oudewater (NL); Jean-Pierre Amorij, Abcoude (NL)

(73) Assignee: De Staat der Nederlanden, vert. door de minister van VWS, Ministerie van Volksgezondheid, Welzijn en Sport, The Hague (NL)

( * ) Notice: Subject to any disclaimer, the term of this patent is extended or adjusted under 35 U.S.C. 154(b) by 9 days.

(21) Appl. No.: 14/382,258

(22) PCT Filed: Mar. 5, 2013

(86) PCT No.: PCT/NL2013/050139
§ 371 (c)(1),
(2) Date: Aug. 29, 2014

(87) PCT Pub. No.: WO2013/133702
PCT Pub. Date: Sep. 12, 2013

(65) Prior Publication Data

US 2015/0030629 A1 Jan. 29, 2015

Related U.S. Application Data

(60) Provisional application No. 61/606,577, filed on Mar. 5, 2012.

(30) Foreign Application Priority Data

Mar. 5, 2012 (EP) .................................... 12158086

(51) Int. Cl.

| | |
|---|---|
| *A61K 39/13* | (2006.01) |
| *A61K 47/02* | (2006.01) |
| *A61K 47/18* | (2017.01) |
| *A61K 47/26* | (2006.01) |
| *A61K 9/19* | (2006.01) |
| *C12N 7/00* | (2006.01) |

(52) U.S. Cl.
CPC ................ *A61K 39/13* (2013.01); *A61K 9/19* (2013.01); *A61K 47/02* (2013.01); *A61K 47/183* (2013.01); *A61K 47/26* (2013.01); *C12N 7/00* (2013.01); *C12N 2770/32634* (2013.01)

(58) Field of Classification Search
None
See application file for complete search history.

(56) References Cited

U.S. PATENT DOCUMENTS

| | | | | |
|---|---|---|---|---|
| 4,500,512 A * | 2/1985 | Barme | A61K 9/19 | 424/218.1 |
| 2008/0311078 A1* | 12/2008 | Gokarn | A61K 9/08 | 514/1.1 |

FOREIGN PATENT DOCUMENTS

| | | | |
|---|---|---|---|
| EP | 2 322 211 | A1 | 5/2011 |
| WO | WO-99/12568 | A1 | 3/1999 |
| WO | WO-02/13858 | A1 | 2/2002 |
| WO | WO-2005/058356 | A2 | 6/2005 |
| WO | WO-2006/094974 | A2 | 9/2006 |
| WO | WO-2011/072218 | A2 | 6/2011 |

OTHER PUBLICATIONS

Kraan et al. Pharm Res. Oct. 2014;31(10):2618-29.*
Kraan et al. 2016 Vaccine vol. 34(38) pp. 4572-4578.*
Shiomi et al., "Heat stability of the lyophilized sabin poliovaccine", Jpn. J. Infect. Dis., 2003, vol. 56, pp. 70-72.
Carpenter, J.F. et al., "Interactions of stabilizing additives with proteins during freeze-thawing and freeze-drying", Dev Biol Stand, vol. 74, 1992, pp. 225-238, 238-239.
International Search Report of PCT/NL2013/050139 dated Apr. 17, 2013.

* cited by examiner

*Primary Examiner* — Shanon A Foley
*Assistant Examiner* — Myron Hill
(74) *Attorney, Agent, or Firm* — Gilberto M. Villacorta; Sunit Talapatra; Foley & Lardner LLP

(57) ABSTRACT

The present invention relates to methods for producing dried formulations of biopharmaceutical agents that aim to minimize the loss of activity of the agents upon drying and to provide dried formulations with an extended shelf life. The method comprises the step of drying an aqueous solution comprising, in addition to the biopharmaceutical agent, at least an amino acid, a polyol and a metal salt. Preferably the amino acid is glutamate, the polyol is sorbitol and optionally also mannitol and the metal salt is a magnesium salt. The solution is dried by vacuum drying or by lyophilization. The methods are particularly useful for preparing dried formulations of viruses such as poliovirus or respiratory syncytial virus to be used for vaccination. The invention also relates to dried formulations prepared in accordance with the methods of the invention and to their use as medicaments, e.g. as vaccines.

16 Claims, 20 Drawing Sheets

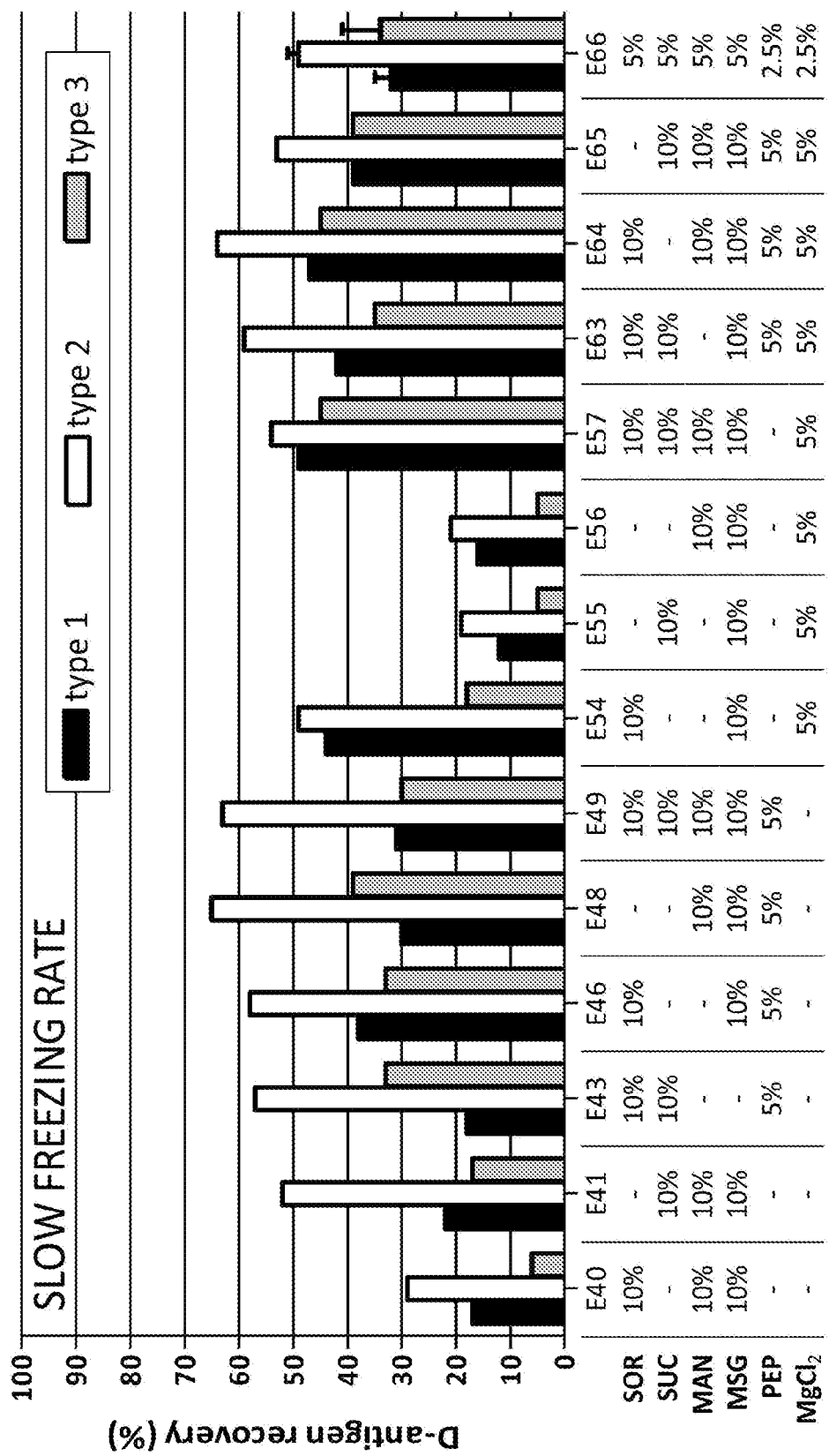

METHODS AND COMPOSITIONS FOR STABILIZING DRIED BIOLOGICAL MATERIALS

CROSS REFERENCE TO RELATED APPLICATIONS

The present application is a National Stage of International Application No. PCT/NL2013/050139 filed on Mar. 5, 2013, published as WO 2013/133702, which claims priority to European Application No. 12158086.4 and U.S. Provisional Application No. 61/606,577, both filed Mar. 5, 2012. The contents of these applications are herein incorporated by reference in their entirety.

FIELD OF THE INVENTION

The present invention relates the methods and compositions for stabilizing and preserving dried biological materials. These biological materials include lyophilized or vacuum-dried preparations of biopharmaceuticals such as vaccines, in particular viral vaccines. The invention therefore relates to the field of production and formulation of biopharmaceuticals and to the field of vaccinology.

BACKGROUND OF THE INVENTION

The long-term storage of biological compounds poses a unique challenge, considering that these compounds are usually fragile and vulnerable. Very few biological compounds are sufficiently stable in liquid environment, in solution or suspension, to allow them to be isolated, purified and stored at unrefrigerated conditions, especially at room temperature or higher temperatures as a solution for anything more than a short period of time.

One way to improve the stability of biopharmaceuticals is by converting them into a dry state [17]. Both commercially and practically, storage of biological compounds in dry form carries with it enormous benefits. Successfully dried reagents, materials and tissues have reduced weight and require reduced space for storage not withstanding their increased shelf life. This is not only of use for the final product, like in final lots of vaccines for use within 3 months to 2 year, but also for stockpiling (1-50 year or more years of storage) seedlots, bulks or final lots. Room temperature storage of dried materials is moreover cost effective when compared to low temperature storage options and the concomitant cost. In addition, several routes of delivery, including pulmonary delivery of powders, dermal delivery by coated or dissolving microneedles, parenteral delivery by powders or dissolvable needles depend on sophisticated ways of formulations. There exist several technologies for producing dried biological compounds, including spray drying, vacuum drying, air-drying, coating, foam-drying. One of the oldest and commonly used technique is freeze-drying, also called lyophilization. For a long period of time freeze-drying was seen as more of an art than a science, which hindered a scientific approach and research.

The most commonly used method for preparing solid biopharmaceuticals is lyophilization. This process consists of a freezing step followed by two drying steps, the primary drying where frozen water is removed by sublimation and the secondary drying where the non-frozen 'bound' water is removed. Either freezing or drying stresses can modify the thermodynamic stability of biopharmaceuticals and can induce or facilitate protein unfolding. Unfolding can lead to irreversible denaturation of the biopharmaceutical, but may also reduce the storage stability in the dry state [19]. For a stable lyophilisate, excipients serving as stabilizer and/or bulking agents are used. Different compounds, such as sugars, polymers, amino acids and surfactants, have been shown to improve the stability of biopharmaceuticals during lyophilization and subsequent storage [18, 20]. In literature several mechanisms are described how excipients are believed to protect biopharmaceuticals like proteins and vaccines, during freezing, drying and subsequent storage. Understanding the cryo- and lyoprotection mechanisms of different stabilizers is important in the development of a rational formulation and process design for a stable lyophilized vaccine [21].

During freezing, the physical environment of a biopharmaceutical changes dramatically leading to the development of stresses that impact the integrity of the proteinaceous biopharmaceutical. The most critical stresses to which a biopharmaceutical is exposed during freezing are low temperature, freeze-concentration and the formation of ice [18, 19, 21, 22]. Cold denaturation is the phenomenon whereby biopharmaceuticals lose their compact folded structure as a result of a temperature drop. The currently accepted explanation for cold denaturation is based on a change in the contact free energy between water and non-polar groups at colder temperatures, which would weaken the hydrophobic interaction and thus disrupt biopharmaceutical structure [19, 20, 23]. Due to ice formation, the concentration of all solutes increases dramatically during freezing. All changes related to concentration, such as ionic strength, crystallization of solutes and phase separation, may potentially destabilize a biopharmaceutical [21].

The initial relative composition and pH of the formulation can circumvent detoriation of the biopharmaceutical by freezing stresses. For example, it has been found with many biopharmaceuticals that increasing the biopharmaceutical concentration in the formulation relatively to other excipients before freezing will increase the stability of the biopharmaceutical during freeze-thawing [24]. Similarly, an initial pH that is optimal for the biopharmaceutical in solution will give the highest recovery of intact biopharmaceutical after freeze-thawing [20].

Even after optimization of all these factors, many biopharmaceuticals still denaturize during freeze-thawing, therefore additives are needed to minimize protein/biopharmaceutical denaturation. Different excipients that come from very dissimilar chemical classes are able to give cryoprotection. According to the 'solute exclusion hypothesis', cryoprotectants have been shown to preferentially not to be in contact with the surface of biopharmaceuticals in aqueous solutions [24]. The thermodynamic phenomenon of solute exclusion in the presence of various biopharmaceuticals has been determined for various excipients, such as salts, amino acids, methylamines, polyethylene glycols, polyols, surfactants and sugars [19, 21, 24, 25].

The 'vitrification hypothesis' is a widely known kinetic mechanism. According to this mechanism, both freeze-concentration and a temperature drop increase viscosity, reduce mobility and slow all dynamic processes. When the system reaches a glassy state, all molecules in the glass become physically (e.g. denaturation, aggregation) and chemically (e.g. oxidation, hydrolysis, deamidation) immobile and the rate constant of biopharmaceutical degradation is reduced [19, 26].

Ice-water interfaces formed during freezing may cause surface denaturation. Addition of surfactants may drop surface tension of the biopharmaceutical solution and thus reduce biopharmaceutical adsorption and aggregation [25, 27].

Polymers could stabilize biopharmaceuticals by raising the glass transition temperature of the formulation and by inhibiting crystallization of small stabilizing additives, like disaccharides [18, 22]. Amino acids may protect biopharmaceuticals as well from freezing denaturation by reducing the rate and extend of buffer salt crystallization and thus suppressing the pH shift [18].

In an aqueous solution biopharmaceuticals are fully hydrated, which means that the biopharmaceutical has a monolayer of water covering and interacting (by hydrogen bonds) with the biopharmaceutical surface [28]. Drying removes part of the hydration shell and this may disrupt the native state of the biopharmaceutical leading to denaturation. In order to prevent denaturation during drying protectants are required. An important stabilization mechanism of such protectants is called the 'water substitution hypothesis' [18-20, 29]. Sugars, such as sucrose and trehalose, polyols [20, 30] and amino acids [31] are able to form hydrogen bonds with the dried biopharmaceutical. As such they can act as a water substitute, when the hydration shell is removed. The formation of an amorphous glass, explained above as the 'vitrification hypothesis', is also a major protection mechanism.

In addition to water substitution and glass formation, many excipients, especially polymers can stabilize biopharmaceuticals by increasing the glass transition temperature ($T_g$), which is defined as the transition temperature between the rubbery (liquid-like) and glassy (solid-like) states. Generally, the higher the $T_g$, the lower the molecular mobility in the glass (e.g. movement of the biopharmaceutical, stabilizing compounds, oxygen and water) and the more stable the biopharmaceutical formulation during drying and subsequent storage [18, 22]. Another mechanism involved in the stabilization of biopharmaceuticals during drying and that is applicable for polysaccharides and other polymers, is the inhibition of crystallization during solute concentration of small excipients that stabilize the biopharmaceutical during drying.

Due to their preference for the bulk environment instead of the biopharmaceutical surface (previously named as 'solute exclusion'), some excipients are able to act as bulking agent, which means that they provide mechanical support to the final cake, improve product elegance, and prevent product collapse during drying. Mannitol and glycine are frequently used bulking agents, because of their non-toxicity, high solubility, and high eutectic temperature [18, 25, 32]. Most amino acids are potential bulking agents as well as they easily crystallize [33].

If the biopharmaceutical is stable during the drying process, then long-term storage in the dried state is often feasible. Although in general the drying process itself is most detrimental to the biopharmaceutical, dried biopharmaceuticals may still loss their structure or potency during storage if not properly formulated. Aggregation is a major physical instability for biopharmaceuticals during storage. Different chemical degradations, like deamidation, oxidation and hydrolysis, may occur as well during storage, but these alterations may not necessarily affect the activity of biopharmaceutical, depending on the location of the transformed residue(s). Reducing sugars such as glucose and sucrose can react with lysine and arginine residues in biopharmaceuticals to form carbohydrate adduct via the Maillard reaction, a browning reaction, which can lead to a significant loss of activity of the lyophilized biopharmaceutical during storage.

Storage temperature is one of the most important factors affecting the stability of biopharmaceuticals in the solid state. Other factors that affect long-term storage stability are the glass transition temperature ($T_g$) of the formulation, formulation pH and the residual moisture content after drying. The moisture content of a dried formulation may change significantly during storage due to several factors, including stopper moisture release, crystallization of an amorphous excipients or moisture release from an excipient hydrate. Excipients that are used to stabilize biopharmaceuticals during drying may destabilize biopharmaceuticals in the solid state if their quantities are not appropriately used in the formulation. Also the risk of crystallization of amorphous excipients exist during storage, because the crystalline state is thermodynamically more stable than the glassy state [39]. Many sugars and polyols have the tendency to crystallize, but this is strongly affected by their relative amount in the formulation, storage temperature and relative humidity [18, 40]. In addition, the relative composition of several excipients and the presence of non-crystallizing stabilizers, such as polymers, may inhibit crystallization of excipients.

Stabilization mechanisms for biopharmaceuticals in the dry state during long-term storage are similar to those for lyoprotection, including formation of an amorphous glassy state, water substitution, and hydrogen bonding between excipients and the biopharmaceutical [41]. A combination of these mechanisms is required for maximum biopharmaceutical stabilization in the solid state [18, 42]. The final quality of a lyophilized product is determined by the choice of excipients, including buffering, bulking and stabilizing agents, and the lyophilization process.

Poliomyelitis is a highly infectious disease which mainly affects young children. The disease, caused by any one of three serotypes of poliovirus (type 1, type 2 or type 3) has no specific treatment, but can be prevented through vaccination. Currently, the oral poliomyelitis vaccine (Sabin OPV) is the vaccine of choice to strive for global eradication of poliomyelitis. However, a major concern is the ability of OPV to revert to a form that can cause paralysis, so-called vaccine associated paralytic poliomyelitis (VAPP). Another risk of permanent use of live attenuated poliovirus is the reversion to vaccine-derived polioviruses (VDPV) [1]. In Western countries the use of an inactivated Salk polio vaccine (IPV) is the current preferred way to eliminate the risk of VAPP and circulating VDPV. IPV is thought to be most suitable for continuation of the global eradication program [1-3].

To achieve global polio eradication an (improved) IPV must be efficacious, inexpensive, safe to manufacture, and easy to administer [4]. The feasibility of current IPV in developing countries is limited, because IPV is more expensive than OPV and is administered through injections only [1, 3, 5]. In order to limit the expenses of IPV, WHO and RIVM are developing a non-commercial IPV for technology transfer to developing countries. Because the containment of the wild-type Salk polio virus during production might be an issue, especially in developing countries, the new vaccine will be based on the OPV strain, Sabin (sIPV), for which the production costs is also expected to be less expensive For further reduction in costs, RIVM is developing sIPV formulations that show dose sparing by using an adjuvant and/or other immunization routes [6].

Since alternative delivery methods and improved vaccine formulations have the potential to make vaccine delivery easier and safer [7, 8], currently several alternative vaccine delivery methods are being developed.

It appears that there are differences in heat stability between the various inactivated polio serotypes, with type 1 being the most vulnerable. In the absence of any preservative type 1 deteriorates slowly after storage for two years at 4° C., while type 2 and 3 remain potent for many years. The D-antigen content drops significantly after 20 days at 24° C. and is undetectable after exposure to 32° C. for the same period. In contrast, no significant changes in D-antigenicity were observed for type 2 at either of these temperatures. Type 3 remains stable for 20 days at 24° C., but the D-antigen content drops significantly at 32° C. [9].

All three serotypes of IPV show satisfactory maintenance of potency when incorporated into combined vaccines and stored at 4° C. for periods ranging from one year to over four years, based on observations made on DT-polio vaccine, which is preserved with 2-phenoxy-ethanol and adsorbed to aluminium hydroxide [9, 10]. Longer storage resulted in a decline in antigenicity, especially for type 1 [9]. The IPV as stand-alone vaccine is stable for 4 years at 4° C. and one month at 25° C. [10]. At 37° C. there is a significant loss of potency of type 1 after 1-2 days and of types 2 and 3 after two weeks [11, 12]. Also freezing has a negative effect on the potency of IPV, which is related to loss of the D-antigen structure [12].

After polio eradication a stockpile of polio vaccines is required to anticipate on the potential risk of new polio outbreaks caused by circulating VDPV (even after OPV cessation) [13-15] or bioterrorism attacks. In order to achieve an optimal vaccine stockpile various issues need to be considered. The shelf-life is an important detail, because a delayed expiration time will reduce the stockpile costs [16]. To guarantee the potency of vaccines for many years the shelf-life of vaccines such as IPV needs to be extended. There is thus a need for improved formulations that extend shelf-life of biopharmaceuticals and improved method for producing such formulations, preferably in dry form.

SUMMARY OF THE INVENTION

In a first aspect the invention relates to a method for producing a dried formulation of a biopharmaceutical agent, wherein the method comprises drying a solution comprising a biopharmaceutical agent, an amino acid, a polyol, a metal salt and water.

Preferably, in the method of the invention, the solution consists essentially of 1 pg-10 g per ml of the biopharmaceutical agent, 0.01-20% (w/v) of the amino acid, 0.5-20% (w/v) of the polyol, 0.005-10% (w/v) of the metal salt and water. More preferably, the amino acid is glutamate, arginine, histidine, asparagine, glycine or a mixture thereof; the polyol is sorbitol, mannitol, mannose, maltitol or a mixture thereof; and the metal salt is a salt of $Mg^{++}$, $Ca^{++}$ or $Li^+$ or a mixture thereof, of which $Cl^-$ or $SO_4^{2-}$ salts or mixtures thereof are preferred.

In the method of the invention the glutamate is preferably dissolved in the solution in the form of monosodium glutamate.

In a preferred embodiment of the method of the invention, the solution consists essentially of 1 pg-10 g per ml of the biopharmaceutical agent, 5-20% (w/v) sorbitol, 5-20% (w/v) monosodium glutamate, 2-10% (w/v) of a magnesium salt, preferably $MgCl_2$ and/or $MgSO_4$, and optionally 5-20% (w/v) mannitol.

In the methods of the invention, the solution preferably comprises a pharmaceutically acceptable buffer and is buffered at a neutral pH. It is also preferred that the solution is dried by vacuum drying or by lyophilization.

In the methods of the invention, the biopharmaceutical agent preferably is an agent comprising proteinaceous material. More preferably the biopharmaceutical agent is a virus, preferably an Enterovirus or a Pneumovirus. Most preferably, the biopharmaceutical agent comprises poliovirus of serotypes 1, 2 and 3, preferable inactivated poliovirus of serotypes 1, 2 and 3, or wherein the biopharmaceutical agent is a human or bovine RSV.

In a preferred embodiment of the method of the invention, the dried formulation, upon reconstitution after drying, retains at least 50% of the activity of the biopharmaceutical agent present in the solution prior to drying. In another embodiment of the method of the invention, wherein the solution to be dried comprises more than one different biopharmaceutical agents and wherein the difference in loss of activities for the different agents preferably is less than 50%, whereby the retained activity of the agent with the most loss in activity is expressed as percent of the retained activity of the agent with the least loss, which is set at 100%.

In a preferred embodiment of the method of the invention, the dried formulation upon reconstitution after storage for at least one week at 45° C., retains at least 50% of the activity of the biopharmaceutical agent present in the solution prior to drying. In another embodiment of the method of the invention, wherein the dried formulation comprises more than one different biopharmaceutical agents and wherein the difference in loss of activities for the different agents preferably is less than 50%, whereby the retained activity of the agent with the most loss in activity is expressed as percent of the retained activity of the agent with the least loss, which is set at 100%.

In a second aspect, the invention pertains to a dried formulation of a biopharmaceutical agent obtainable in any the method according to the invention.

In a third aspect, the invention pertains to the formulation according to the invention for use as a medicament, preferably for inducing an immune response (in an individual) against an infectious disease or a tumour.

DESCRIPTION OF THE INVENTION

In a first aspect, the invention relates to a method for producing a dried formulation of a biopharmaceutical agent. The methods of the invention are aimed at achieving at least two improvements: 1) minimizing the loss of activity of the biopharmaceutical agent upon drying of the formulation (and preferably subsequent reconstitution of the dried formulation); and, 2) increasing the stability, i.e. shelf-life of the dried formulation of the biopharmaceutical agent, i.e. minimizing the loss of activity of the biopharmaceutical agent upon storage of the dried formulation. The method preferably comprises the step comprises drying a aqueous solution comprising a biopharmaceutical agent and one or more of an amino acid, a polyol and a metal salt.

In the method of the invention, the solution to be dried comprises, consists essentially of, or consists of: a) the biopharmaceutical agent as specified herein below and in a concentration specified herein below; b) the amino acid as specified herein below and in a concentration specified herein below; c) the polyol as specified herein below and in a concentration specified herein below; d) the metal salt as specified herein below and in a concentration specified herein below; e) water; optionally, f) a buffer as specified herein below, in a concentration specified herein below and at a pH specified herein below; and, optionally, g) further ingredients as specified herein below and in a concentration specified herein below.

The Biopharmaceutical Agent

A "biopharmaceutical agent" is herein understood to refer to a biological agent, which is physiologically active when applied to a mammal, especially when applied to a human patient, preferably in a pharmaceutically acceptable form. The biological agent preferably is an agent that is produced by or obtainable from a cell, although synthetic copies of agents obtainable from a cell and chemically modified agents obtainable from a cell are included in the term biological agent. The biological agent can be a protein-based agent, i.e. an agent comprising proteinaceous material such as proteins, polypeptides and peptides. The biological agent may further comprises or consist of nucleic acid, e.g. DNA, RNA or a nucleic acid analogue.

A preferred biopharmaceutical agent is a virus or a virion, preferably a virus that infects mammals, preferably a virus that infects humans. The virus can be an enveloped virus but preferably is a non-enveloped virus. It is understood herein the term 'virus' as used herein include wild type viruses as they occur in nature (e.g. natural isolates), as well as 'man-made' attenuated, mutant and defective viruses. The term 'virus' also includes recombinant viruses, i.e. viruses constructed using recombinant DNA technology, such as defective viruses, e.g. lacking (parts of) one or more viral genes and gene therapy vectors wherein part of the viral genome is replaced with one or more gene(s) of interest. A preferred virus is Picornavirus, more preferably an Enterovirus, such as poliovirus, Coxsackievirus, echovirus and rhinovirus. Most preferably the virus is poliovirus. The poliovirus can be an attenuated poliovirus but preferably is inactivated poliovirus (IPV). The poliovirus can also be an inactivated attenuated poliovirus The biopharmaceutical agent can comprise one or more of the polio viral serotypes 1, 2 and 3 but preferably the agent comprise all three polio viral serotypes 1, 2 and 3. Suitable strains of serotype 1 poliovirus include but are not limited to one or more of the Sabin 1, Mahoney, Brunhilde, CHAT and Cox strains. Suitable strains of serotype 2 poliovirus include but are not limited to one or more of the Sabin 2, MEF-1 and Lansing strains. Suitable strains of serotype 3 poliovirus include but are not limited to one or more of the Sabin 3, Saukett H and G, and Leon strains. In a preferred embodiments the biopharmaceutical agent is a trivalent inactivated polio vaccine such as e.g. the Salk-IPV, containing the inactivated polio viral Mahoney strain for type 1, the inactivated polio viral MEF-1 strain for type 2 and the inactivated polio viral Saukett strain for type 3, or sIPV, containing the inactivated polio viral Sabin-1, -2 and -3 strains. Methods for inactivating polio viral strains for safe use in vaccines are well known in the art and include e.g. inactivation using formalin or beta-propiolactone (see e.g. Jonges et al., 2010, J. Clin. Microbiol. 48:928-940).

In another embodiment biopharmaceutical agent is a virus or a virion of a pneumovirus. The pneumovirus preferably is a Respiratory Syncytial Virus (RSV), more preferably a human or bovine RSV. The human RSV may either be a subgroup A or B virus, and preferably is a clinical isolate, more preferably an isolate that has not been extensively passaged in vitro (preferably passaged less than 10, 8, 6 or 5 times). Preferably the (human or bovine) RSV virus is a virus comprising a viral genome having a deleted or inactivated G attachment protein gene, e.g. having a mutation in its viral genome whereby the viral genome does not encode a functional G attachment protein, such as e.g. the RSV ΔG and RSV ΔG+G virions as described in WO 2005/061698 and in Widjojoatmodjo et al. (2010, Virol. J., 7:114).

The biopharmaceutical agent is preferably present in the solution to be dried in an amount ranging between $1 \times 10^0$ and $1 \times 10^{25}$ live and/or dead or inactivated particles per ml. The number of live particles may be determined by e.g. plaque forming units, cell culture or tissue culture 50% infectious dose ($CCID_{50}$ or $TCID_{50}$) and other suitable virological assays for determining the titer of the agent. The number of dead or inactivated particles may be determined using an assay that quantifies the amount of antigen, such e.g. protein assays, or assays that determine haemagglutination units or polio D-antigen units. Preferably the biopharmaceutical agent is present in the solution in an amount of at least $1 \times 10^1$, $1 \times 10^2$, $1 \times 10^3$, $1 \times 10^3$, $1 \times 10^4$, $1 \times 10^5$, $1 \times 10^6$, $1 \times 10^7$, $1 \times 10^8$, $1 \times 10^9$ or $1 \times 10^{10}$ live and/or dead or inactivated particles per ml and/or in an amount of up to $1 \times 10^{24}$, $1 \times 10^{23}$, $1 \times 10^{22}$, $1 \times 10^{21}$, $1 \times 10^{20}$, $1 \times 10^{19}$, $1 \times 10^{18}$, $1 \times 10^{17}$, $1 \times 10^{16}$, $1 \times 10^{15}$ or $1 \times 10^{14}$ live and/or dead or inactivated particles per ml.

The amount of the biopharmaceutical agent in the solution to be dried can also be expressed as weight of the biopharmaceutical agent per ml of the solution. Preferably the biopharmaceutical agent is present in the solution in a weight/ml ranging between 1 pg/ml and 10 g/ml. More preferably, the biopharmaceutical agent is present in the solution in an amount of at least $10^{-11}$, $10^{-10}$, $10^{-9}$, $10^{-8}$, $10^{-7}$, $10^{-6}$, $10^{-5}$, $10^{-4}$, g/ml and/or in an amount of up to $10^{-3}$, $10^{-2}$, $10^{-1}$, or $10^0$ g/ml. The weight of the biopharmaceutical agent in the solution may be determined by means known in the art per se, including e.g. protein assays. The aforementioned weights of the biopharmaceutical agent may thus also be expressed as grams protein per ml to be determined in a suitable protein assay (e.g. the Bradford assay; Zor and Selinger, 1996, Anal. Biochem. 236: 302-308).

In a preferred embodiment wherein the biopharmaceutical agent is poliovirus, the amount of poliovirus in the solution preferably is at least 0.01, 0.1, 1.0, or 10 DU/ml and up to 10.000, 1.000 or 100 DU/ml, wherein 1 DU is defined and determined with a QC-ELISA as described by Westdijk et al. [6]. In an embodiment wherein the biopharmaceutical agent comprises a multivalent poliovirus (vaccine), it is understood that each polio viral serotype is present in an amount of at least 0.01, 0.1, 1.0, or 10 DU/ml and up to 10.000, 1.000 or 100 DU/ml.

In a preferred embodiment wherein the biopharmaceutical agent is RSV, the amount of RSV in the solution preferably is at least $1 \times 10^1$, $1 \times 10^2$, $1 \times 10^3$, $1 \times 10^3$, $1 \times 10^4$ $TCID_{50}$/ml and up to $1 \times 10^{25}$, $1 \times 10^{29}$, $1 \times 10^{15}$, $1 \times 10^{12}$, $1 \times 10^{10}$ or $1 \times 10^9$ $TCID_{50}$/ml, wherein the $TCID_{50}$ for RSV is defined and determined as described by Widjojoatmodjo et al. (2010, Virol. J., 7:114).

The Amino Acid

The amino acid in the solution to be dried can be any D- or L-amino acid that is pharmaceutically acceptable. Such amino acids include the 20 standard 'proteinogenic' or 'natural' amino acids (histidine, alanine, isoleucine, arginine, leucine, asparagine, lysine, aspartic acid, methionine, cysteine, phenylalanine, glutamic acid, threonine, glutamine, tryptophan, glycine, valine, proline, tyrosine and serine), as well as non-natural amino acid such as e.g. ornithine, citrulline, selenocysteine, taurine and pyrrolysine. Preferably the amino acid in the solution to be dried is one or more of glutamate, glutamine, arginine, histidine, asparagine, lysine, leucine and glycine, more preferably one or more of glutamate, arginine and histidine. The solution to be dried may thus comprise a mixture of amino acids. The amino acid(s) in the solution to be dried may be either optical D- or L-isomers or mixtures thereof, although preferably the amino acid(s) are L-isomers.

In a preferred embodiment, the amino acid in the solution to be dried is one or more of L-glutamate, L-arginine and L-histidine. L-glutamate may also be in the form of Na-glutamate, peptone, non-animal peptone, vegetable peptone. L-arginine may also be in the form of poly-L-arginine, peptone, non-animal peptone, vegetable peptone. L-histidine may also be in the form of Na-histidine. L-lysine may also be in the form of poly-L-lysine.

In a particularly preferred embodiment, the amino acid in the solution to be dried comprises glutamate. The glutamate can be one or more of sodium glutamate, potassium glutamate, ammonium glutamate, calcium diglutamate, magnesium diglutamate and glutamic acid. More preferably, the glutamate is dissolved in the solution in the form of monosodium glutamate (MSG).

The amino acid(s) preferably are present in the solution to be dried in a concentration in the range of 0.01-20% (w/v), i.e. percent weight per volume of the solution. Thus, preferably, the amino acid(s) are present in the solution to be dried in a concentration of at least or more than 0.01, 0.02, 0.05, 0.1, 0.2, 0.5, 1.0, 2.0, 5.0, 8.0, 9.0 or 9.5% (w/v) and/or the amino acid(s) are present in the solution to be dried in a concentration of no more or less than 20.0, 17.5, 15.0, 12.5, 11.0 or 10.5% (w/v). Most preferably the amino acid(s) are present in the solution to be dried in a concentration of about 10% (w/v).

The Polyol

The polyol in the solution to be dried preferably is a sugar or sugar alcohol. Preferred sugars include sucrose, trehalose, mannose and dextran. Preferred sugar alcohols include sorbitol, mannitol and matltitol. Preferably the solution to be dried comprises at least one or more of sorbitol, mannose, mannitol and matltitol, more preferably, at least one or more of sorbitol, mannose, and mannitol, still more preferably at least one or both of sorbitol and mannitol. Most preferably the solution to be dried comprises as polyol at least sorbitol, optionally in combination with mannitol.

In one embodiment the polyol(s) are preferably present in the solution to be dried in a concentration in the range of 0.1-20% (w/v), i.e. percent weight per volume of the solution. Thus, preferably, the polyol(s) are present in the solution to be dried in a concentration of at least or more than 0.1, 0.2, 0.5, 1.0, 2.0, 5.0, 8.0, 9.0 or 9.5% (w/v) and/or the polyol(s) are present in the solution to be dried in a concentration of no more or less than 20.0, 17.5, 15.0, 12.5, 11.0 or 10.5% (w/v). Most preferably, in this embodiment, the polyol(s) are present in the solution to be dried in a concentration of about 10% (w/v). The concentrations in this embodiment are e.g. suitable when sorbitol is used as polyol.

In another embodiment the polyol(s) are preferably present in the solution to be dried in a concentration in the range of 0.1-40% (w/v), i.e. percent weight per volume of the solution. Thus, preferably, the polyol(s) are present in the solution to be dried in a concentration of at least or more than 0.1, 0.2, 0.5, 1.0, 2.0, 5.0, 10.0, 12.5, 15.0 18.0, 19.0 or 19.5% (w/v) and/or the polyol(s) are present in the solution to be dried in a concentration of no more or less than 50.0, 40.0, 35.0, 30.0, 25.0, 22.5, 21.0 or 20.5% (w/v). Most preferably, in this embodiment, the polyol(s) are present in the solution to be dried in a concentration of about 40% (w/v). The concentrations in this embodiment are e.g. suitable when two different polyols are used such as e.g. sorbitol and mannitol. In that case the weight ratio between the two polyols may range from 1:100 to 1:1 including e.g. 1:50, 1:20, 1:10, 1:5, and 1:2.

The Metal Salt

The metal salt dissolved in the solution to be dried can be any pharmaceutically acceptable salt of a divalent or monovalent metal cation. Preferred divalent cations are $Ca^{++}$, $Mg^{++}$ and $Zn^{++}$, of which $Ca^{++}$ and $Mg^{++}$ are more preferred, and of which $Mg^{++}$ is most preferred. Preferred monovalent cations are $Li^+$, $Na^+$ and $K^+$, of which $Li^+$, $Na^+$ are more preferred, and of which $Li^+$ is most preferred. The counter-anion in the metal salt preferably is not an amino acid, preferably not glutamate or aspartate. More preferably, the counter-anion in the metal salt an inorganic anion. Preferred (inorganic) anionic counterions are $Cl^-$, $SO_4^{2-}$ and $CO_3^{2-}$, of which $Cl^-$ and $SO_4^{2-}$ are more preferred, and of which $Cl^-$ is most preferred. The solution can comprise mixtures of one or more of the above metal salts.

The metal salt(s) preferably are present in the solution to be dried in a concentration in the range of 0.005-10% (w/v), i.e. percent weight per volume of the solution. Thus, preferably, the metal salt(s) are present in the solution to be dried in a concentration of at least or more than 0.005, 0.01, 0.02, 0.05, 0.1, 0.2, 0.5, 1.0, 2.0, 3.0, 4.0, or 4.5% (w/v) and/or the metal salt(s) are present in the solution to be dried in a concentration of no more or less than 10.0, 8.0, 7.0, 6.0, or 5.5% (w/v). Most preferably the metal salt(s) are present in the solution to be dried in a concentration of about 5% (w/v).

It is understood that in case the amino acid in the solution to be dried is dissolved in the form of a metal salt of the amino acid, e.g. MSG, the amino acid metal salt is not included in the weight percentage of the metal salt(s) but in the weight percentage of the amino acid(s), whereby the weight of the metal counter cation is included in the weight of the amino acid.

The Buffer

The solution to be dried preferably has a neutral pH, e.g. a pH in the range of 6.0-8.0, or 6.5-7.5 or a pH of about 7.0. The solution to be dried preferably comprises a buffer to maintain the pH at the indicated values. In principle any pharmaceutically acceptable buffer, which preferably has effective buffering capacity in the range of pH values as indicated, can be used in the solution to be dried. The buffer is preferably present in a concentration in the range of 0.5-100 mM, more preferably in the range of 1-50 mM and most preferably in the range of 2-20 mM, such as e.g. about 10 mM.

Suitable buffers for use in the solution to be dried include McIlvaine buffer (see Examples), a citrate buffer, a phosphate buffer, a HEPES buffer and a histidine buffer.

Water

The water used for preparing the solution to be dried preferably is ultrapure and preferably pyrogen-free water, like water for injections.

The concentrations of ingredients (e.g. the excipients) in the solution to be dried of the invention are generally expressed herein as percent weight per volume (w/v) of the solution. This is understood to be the relationship of a solute (e.g. the excipient) to the solvent (e.g. water) expressed as grams of solute per liter of the total solution. For example 50 g of glucose in 1 L of solution, is considered a 5% w/v solution.

In a preferred embodiment, the solution to be dried consists essentially of the biopharmaceutical agent in an amount as defined herein above, 5-20% (w/v) sorbitol, 5-20% (w/v) monosodium glutamate, 2-10% (w/v) of a magnesium salt, preferably $MgCl_2$ and/or $MgSO_4$, optionally 5-20% (w/v) mannitol, and optionally 2-50 mM of a pharmaceutically acceptable buffer which buffers the solution at a neutral pH as indicated herein.

Drying

In the method of the invention, the aqueous solution comprising the biopharmaceutical agent is dried. Any known drying method can be used. A drying method can e.g. be spray drying, air drying, coating, foam-drying, desiccation, vacuum drying, vacuum/freeze drying or freeze-drying, all of which are known to the person skilled in the art per se. In a preferred embodiment, the drying method is vacuum drying or freeze-drying, of which freeze-drying or lyophilization is more preferred.

In one embodiment of a freeze-drying process, the solution to be dried preferably is first frozen to an initial freeze-drying or shelf temperature equal to or lower than of −50° C., −40° C., −30° C., −20° C. or −10° C. A preferred initial shelf temperature is equal to or lower than of −50° C. or −40° C. The solution to be dried may be subjected to fast freezing by immediately placing (a container/vial comprising) the solution on the shelf having an initial shelf temperature as indicated above. Alternatively, the solution to be dried may be subjected to slow freezing by placing (a container/vial comprising) the solution on the shelf having a temperature above 0° C., e.g. 2, 4 or 6° C., and then slowly freezing the solution to the initial freeze-drying temperature as indicated above, by reducing the temperature, preferably at a rate of about 0.5, 1 or 2° C. per minutes. The solution to be dried may be brought to a pressure of 100 microbar or lower. When the set pressure has been reached, the shelf temperature may be increased to higher temperatures. The shelf temperature may e.g. be increased at a rate of e.g. 0.05, 0.1 or 0.2° C. per minute to a temperature of 5, 10 or 15 or ° C. above the initial freeze-drying temperature. The primary drying step is preferably ended when no pressure rise is measured in the chamber. Preferably at that moment, the shelf temperature may be increased to e.g. 5, 10, 15, 20 or 25° C. at a rate of e.g. 0.01, 0.02 or 0.05° C. per minute and optionally in one or more steps. During the secondary drying phase the temperature is preferably kept at this value till no pressure rise can be detected. A preferred freeze-drying process is described in the Examples herein.

In one embodiment of a vacuum-drying process, the solution to be dried preferably is at a temperature in the range of about 5-25° C., e.g. room temperature or more preferably at a temperature in the range of about 10-20° C., e.g. a temperature of about 15° C. The pressure is then reduced, e.g. to a pressure of less than 1, 0.5, 0.2, 0.1, 0.05 mbar. Once under reduced pressure the temperature of the solution being dried can be decreased to a temperature that can be below 0° C. but that is (just) above the eutectic temperature of the solution to prevent freezing of the solution. When no pressure rise is measured in the chamber, the temperature of the solution can be increased to e.g. 5, 10, 15, 20 or 25° C. at a rate of e.g. 0.01, 0.02 or 0.05° C. per minute and optionally in one or more steps. The temperature is preferably kept at this value till no pressure rise can be detected. A preferred vacuum-drying process is described in the Examples herein.

In a second aspect, the invention relates to a dry or dried formulation of a biopharmaceutical agent obtainable or obtained in a method according to the invention as described herein above.

The methods of the invention for producing a dried formulation of a biopharmaceutical agent are preferably aimed at minimizing the loss of activity of the biopharmaceutical agent upon drying of the formulation. Preferably the methods of the invention as well as the formulations themselves are also aimed at minimizing the loss of activity of the biopharmaceutical agent upon subsequent storage of the dried formulation obtainable with the methods of the invention. The methods of the invention are thus preferably methods for producing stable formulations of biopharmaceutical agents, i.e. formulations with a long or extended shelf-life, preferably under refrigerated conditions (e.g. 2-10° C.), at room temperature (e.g. 18-25° C.), or even at elevated temperatures (e.g. 32-45° C.) as may occur in tropical regions.

Loss of activity or inactivation of a biopharmaceutical agent is understood to include both loss of activity due to chemical pathways (such as oxidation, hydrolysis or enzymatic action) as well as physical pathways (such as denaturation, aggregation, gelation). Preferably the loss of activity of the biopharmaceutical agent does not exceed an acceptable level. In other words, at least a level of biological activity or viability and/or a level of original function or structure sufficient for the intended commercial therapeutic and/or diagnostic application of the biopharmaceutical agent is retained after drying and/or subsequent storage.

Depending on the identity of the biopharmaceutical agent, the skilled person will know which assay is to be used for assessing an activity of said biopharmaceutical agent. The activity of the biopharmaceutical agent may be expressed as its viability, e.g. in the case of active live viruses, or activity may be expressed as enzymatic activity or biological activity which may be determined in suitable assays known to the skilled person. In other instances the activity of the may rather relate to the physical and chemical integrity of the agent and may be determined by assessing the structure and/or function of said biopharmaceutical agent. Antigen structure is preferably assessed by ELISA or Biacor analysis. Secondary and tertiary structure is preferably assessed by UV-, fluorescence, Fourier Transformed Infra Red (FTIR) and/or Circular Dichroism (CD) spectroscopy. Immunogenicity is preferably assessed by in vivo analysis using animal models (e.g. mice, rats, cotton rats, ferrets or rabbits). Rats are e.g. a preferred model for poliovirus and cotton rats are a preferred model for RSV.

In a preferred embodiment of the methods of the invention, the drying of the solution (to be dried) causes the dried formulation upon rehydration (preferably immediately) after drying, to retain at least 50, 60, 70, 75, 80, 85, 90 or 95% of the biological activity present in the solution prior to drying. In case more than one biopharmaceutical agent is present in the formulation, the difference in loss of activities for the different agents preferably is less than 50, 60, 70, 75, 80, 85, 90 or 95%, whereby the retained activity of the agent with the most loss in activity is expressed as percent of the retained activity of the agent with the least loss, which is set at 100%.

In another preferred embodiment of the invention, the dried formulation retains at least 50, 60, 70, 75, 80, 85, 90 or 95% of the biological activity present in the solution prior to drying, after storage for at least one week at 45° C. and upon rehydration of the dried formulation. In case more than one biopharmaceutical agent is present in the formulation, the difference in loss of activities for the different agents preferably is less than 50, 60, 70, 75, 80, 85, 90 or 95%, whereby the retained activity of the agent with the most loss in activity is expressed as percent of the retained activity of the agent with the least loss, which is set at 100%. Preferably the percentages of activities retained after storage as indicated above are also retained after storage two weeks, three weeks, four weeks, five weeks, six weeks, seven weeks, eight weeks, nine weeks, ten weeks or more at 37° C. or at 45° C.

In a third aspect the invention relates to a formulation of a biopharmaceutical agent obtainable or obtained in a method according to the invention as described herein above for use as a medicament. For use as a medicament the formulation can be used as dried formulation or it can be reconstituted by dissolving the dried formulation, e.g. using water as defined above. The formulation is preferably reconstituted to its original volume, i.e. the volume before drying. Preferably the formulation is a formulation for inducing an immune response (in an individual) against an infectious disease or a tumour. It is understood that the individual or subject to whom the formulations of the invention are administered can be a human but can also be an animal, such as a farm animal or pet, including e.g. mammals, birds, livestock, poultry, cattle, bovines. More preferably, the formulation is a formulation for vaccination against an infectious disease or tumour. The formulation is thus preferably a formulation for the prevention or treatment of an infectious disease or tumour. In another embodiment the invention relates to the use of the formulation obtainable or obtained in a method according to the invention as described herein above for the manufacture of a medicament for inducing the immune response, for vaccination and/or for the prevention or treatment of an infectious disease or tumour. In yet another embodiment, the invention relates to a method for inducing an immune response against an infectious agent or tumour by administering an effective amount of the formulation to a subject in need thereof. The immune response is preferably induced against an antigen in the biopharmaceutical agent. The antigen preferably is an antigen of a pathogen causing the infectious disease or an antigen of the tumour, or an antigen that induces an immune response against the pathogen or the tumour. The pathogen preferably is a virus as herein defined above. The formulation of the invention can be administered with or without reconstitution via intranasal, parenteral, intramuscular, subcutaneous and/or transdermal routes.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Figure 1:
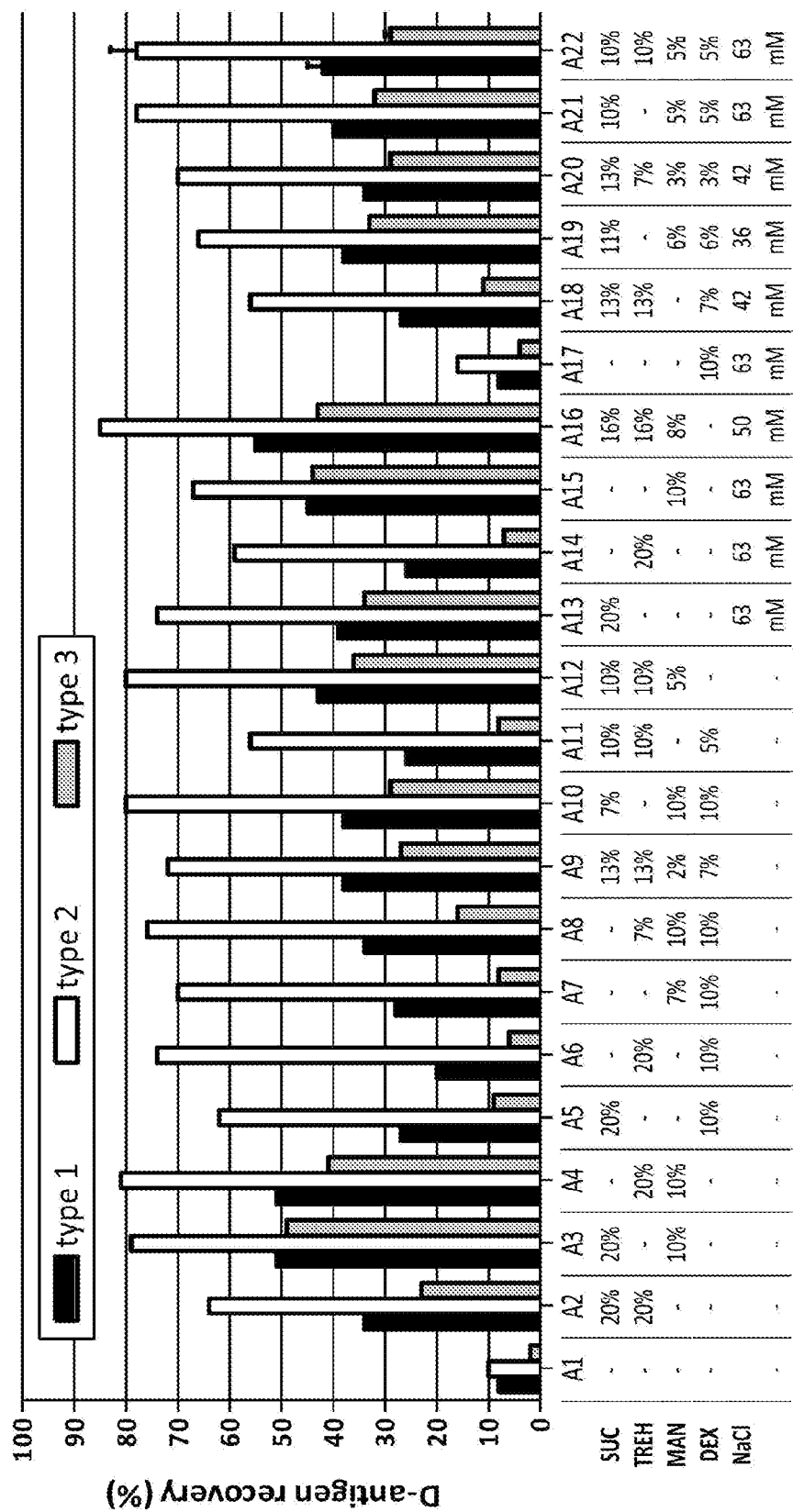
FIG. 1 D-Antigen recovery directly after lyophilization of serotype 1, 2 and 3 IPV-formulations (experiment A). The stabilizing effect of sucrose (SUC), trehalose (TREH), mannitol (MAN), dextran (DEX) and sodium chloride (NaCl) was tested.
Figure 2:
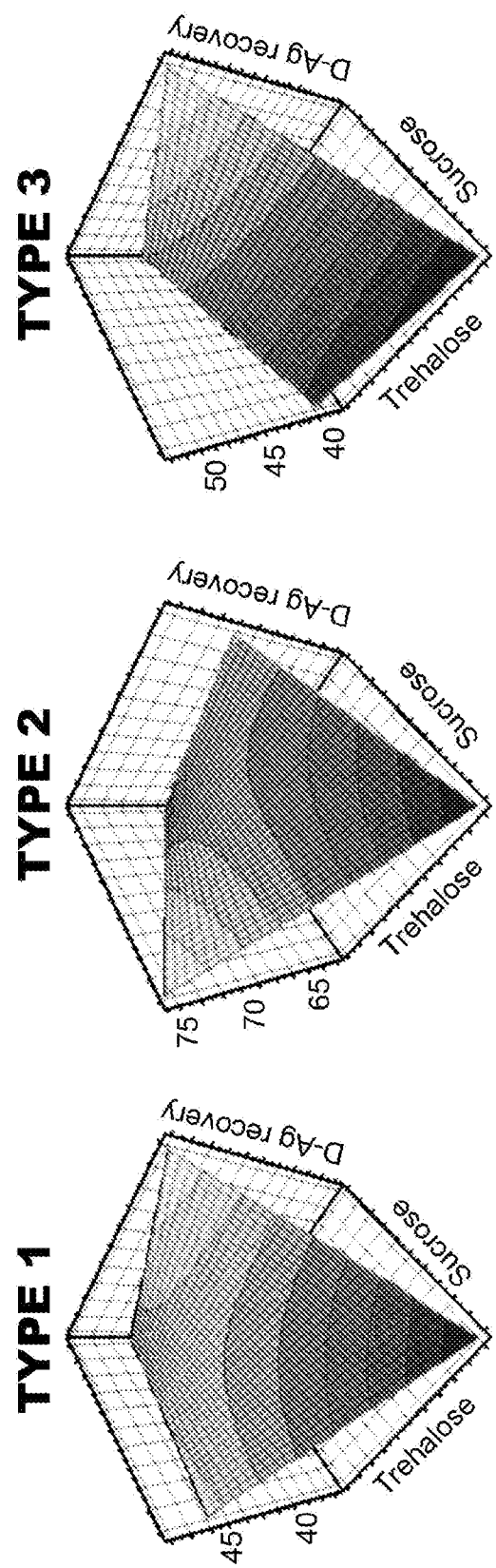
FIG. 2 Response surface plots representing D-antigen recovery percentages of the three serotypes directly after lyophilization of IPV-formulations containing 10% of mannitol and 0% dextran.
Figure 3:
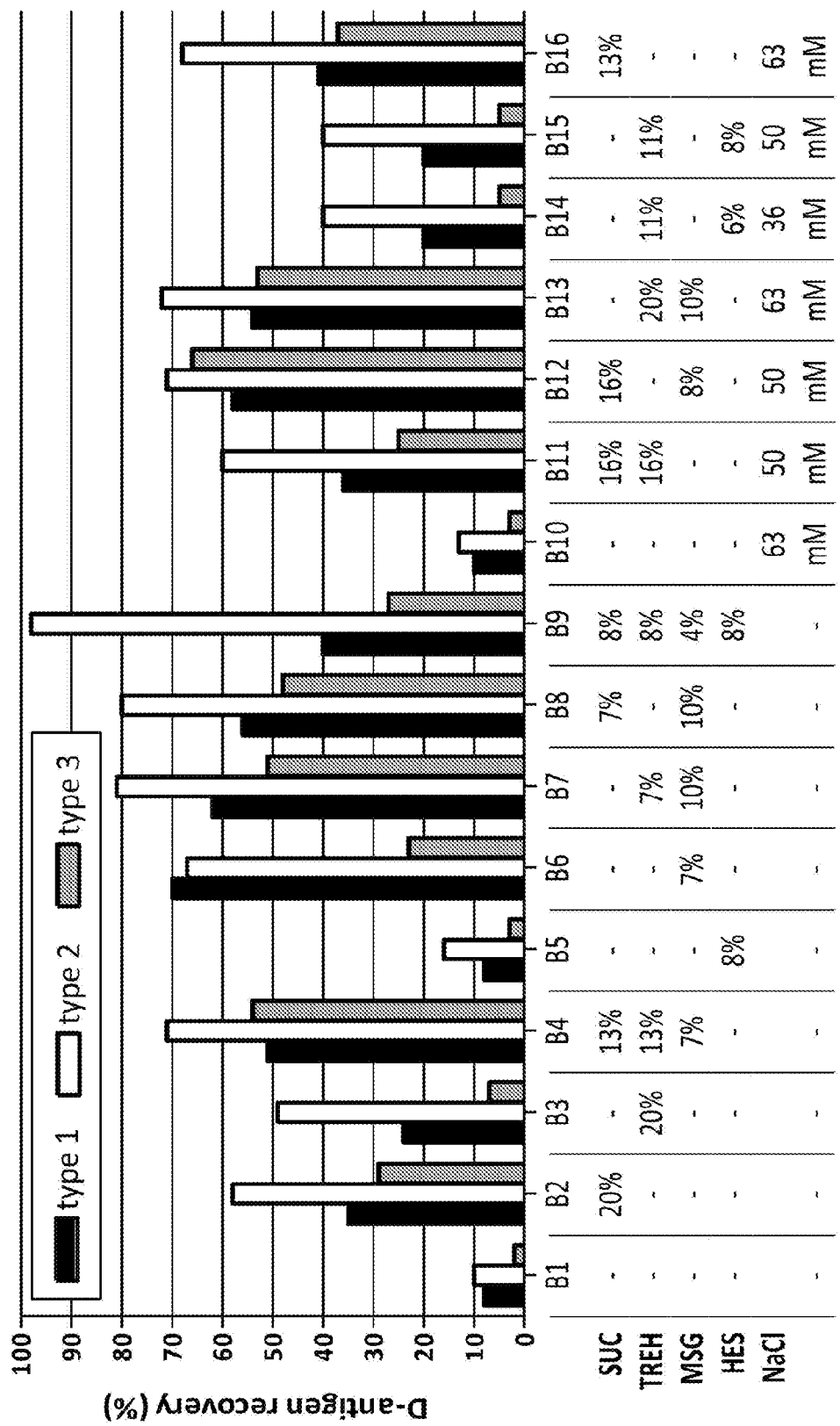
FIG. 3 D-Antigen recovery directly after lyophilization of serotype 1, 2 and 3 IPV-formulations (experiment B). The stabilizing effect of sucrose (SUC), trehalose (TREH), mono-sodium glutamate (MSG), hydroxyethyl starch (HES) and sodium chloride was tested.
Figure 4:
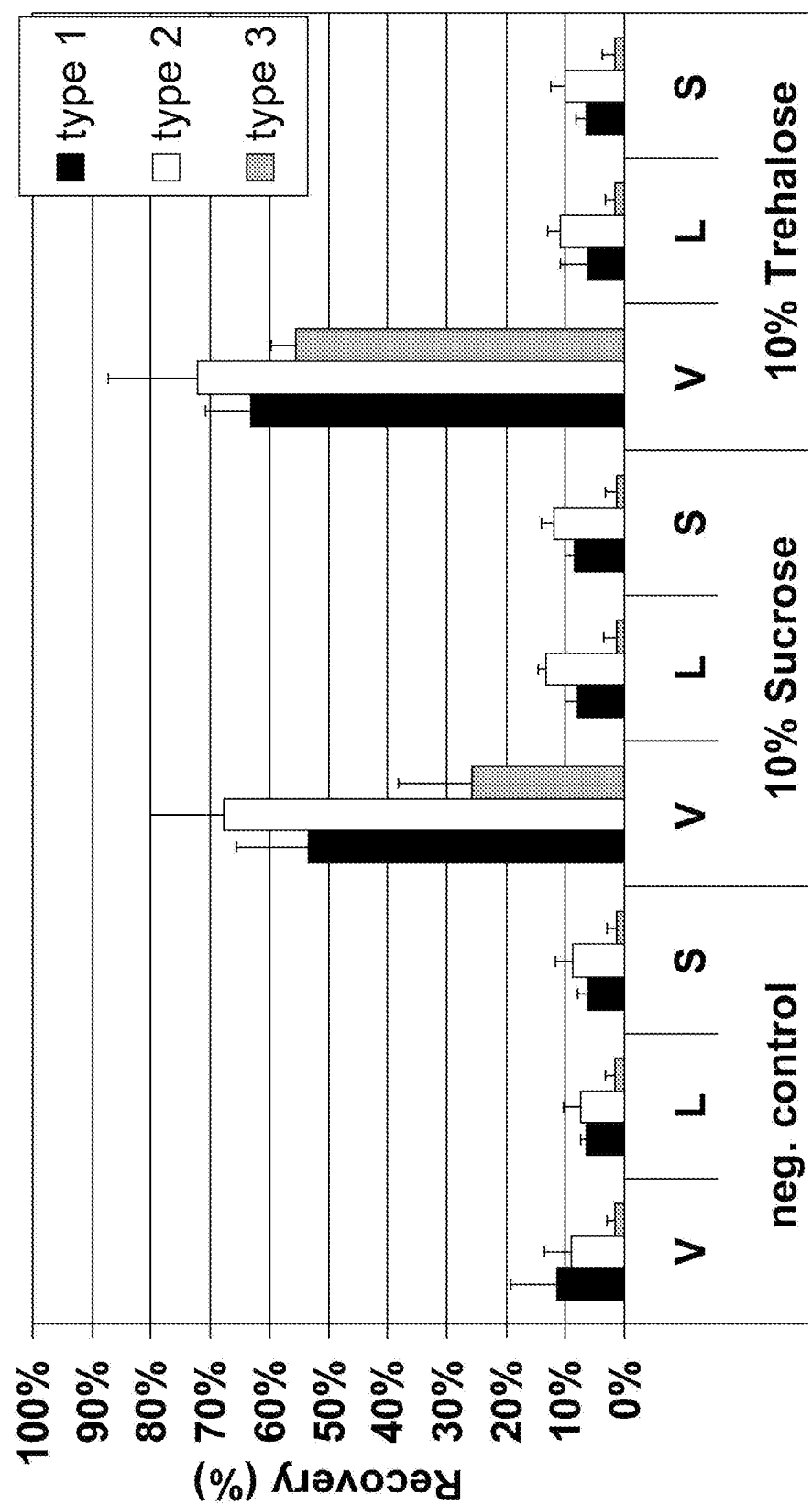
FIG. 4 D-Antigen recovery directly after vacuum drying (V), lyophilization with a slow freezing rate (L) and lyophilization with a fast freezing rate (S). The stabilizing effect of sucrose and trehalose, compared to IPV vaccine without addition of stabilizers (negative control) was investigated.
Figure 5:
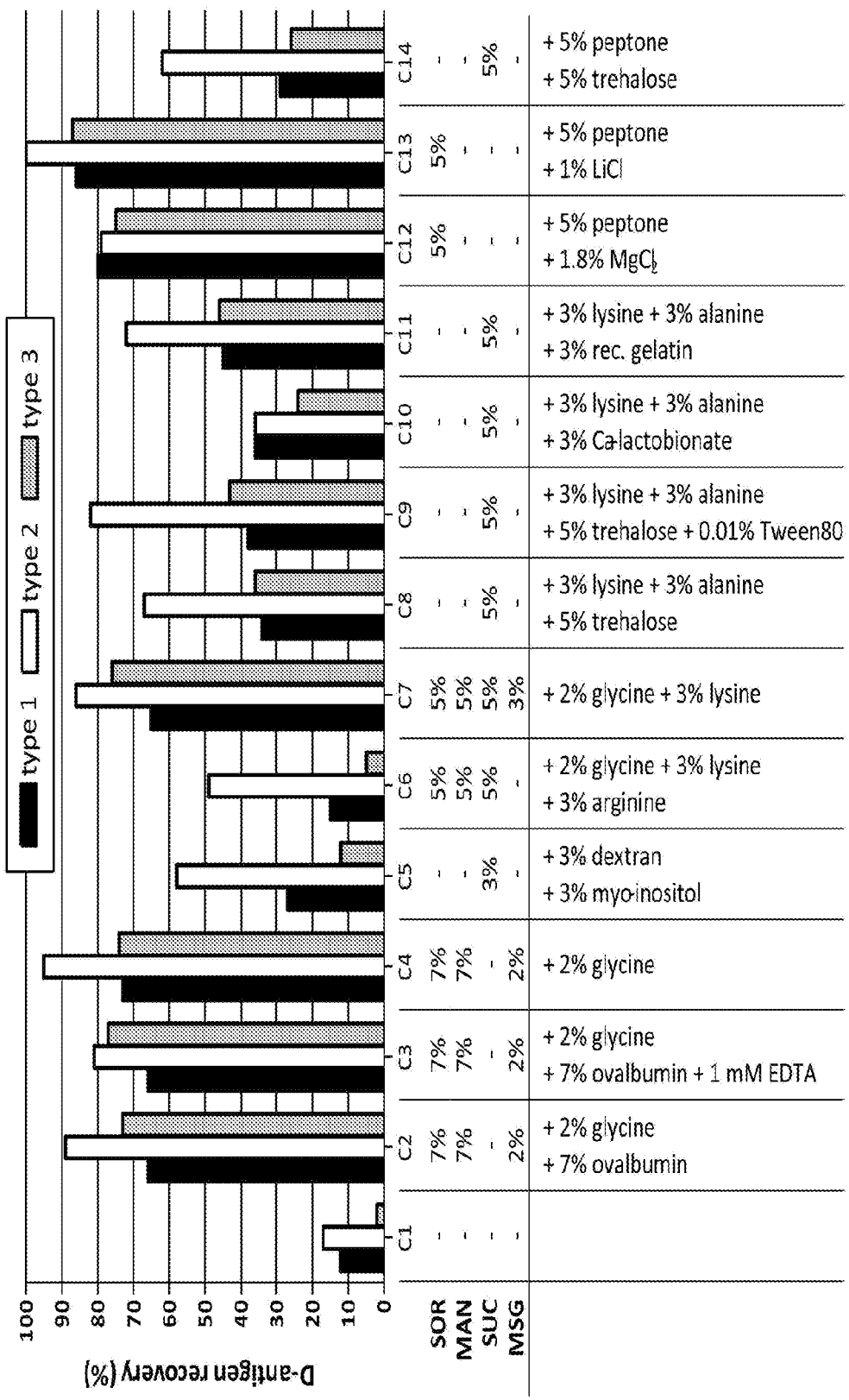
FIG. 5 D-antigen recovery directly after lyophilization of serotype 1, 2 and 3 IPV-formulations as indicated (experiment C).

1. Materials and Methods
1.1 Materials

The trivalent inactivated polio vaccine (Salk-IPV), containing the inactivated Mahoney strain for type 1, MEF for type 2 and Saukett for type 3, was obtained from the process development department of the RIVM-Vaccinology (Bilthoven, The Netherlands). The Salk-IPV trivalent bulk (10×) was formulated as a ten times concentrated 40-8-32 DU/single human dose (1 ml). The concentration of the IPV 05-126B bulk that was used in this study was determined at 411-90-314 DU/ml with the QC-ELISA as described by Westdijk et al. [6].

The excipients sucrose, D-sorbitol, D-trehalose dihydrate, D-glucose monohydrate, mannitol, L-glutamic monosodium salt monohydrate (referred to as glutamate, sodium glutamate, monosodium glutamate or MSG herein), myo-inositol, D-raffinose, hydroxy ethyl starch, glycine, L-proline, L-leucine, calciumchloride dihydrate, maltitol, magnesiumchloride hexahydrate, lithium chloride, and ovalbumin were all purchased from Sigma (St. Louis, Mo.). Peptone (vegetable), dextran (6 kDa, from Leuconostoc ssp), L-histidine, L-alanine, zinc chloride, calcium lactobionate monohydrate were from Fluka (Buchs, Switzerland). Lactitol (Lacty®-M) was from Purac Biochem (Gorinchem, The Netherlands), L-arginine (EP, non-animal origin) and Tween80 were from Merck (Darmstadt, Germany), polyvinylpyrrolidone 25 (PVP, 29 kDa) was from Serva Feinbiochemica GmbH (Heidelberg, Germany), Sol-U-Pro, a hydrolyzed porcine gelatin, was from Dynagel Inc. (Calumet City, Ill.) and Ficoll was from Pharmacia (Uppsala, Sweden). As buffer components sodium dihydrogen phosphate dihydrate ($NaH_2PO_4$), sodium chloride (NaCl), potassium dihydrogen phosphate ($KH_2PO_4$) and EDTA from Merck were used. Trisodium citrate dihydrate, citric acid and HEPES were from Sigma-Aldrich (St. Louis, Mo.) and disodium hydrogen phosphate dihydrate ($Na_2HPO_4$) was from Fluka (Buchs, Switzerland). All excipients used were of reagent quality or higher grade.

To prepare 10 mM McIlvaine buffer, 10 mM citric acid was added to 10 mM $Na_2HPO_4$ in a ratio of 1:6 and a pH-value of 7.0. For the 10 mM citrate buffer the components trisodiumcitrate dihydrate (10 mM) and citric acid (10 mM) were mixed together till pH 7.0 was reached. The 10 mM phosphate buffer of pH 7.0 consisted of 10 mM $KH_2PO_4$ and 10 mM $Na_2HPO_4$. The 10 mM HEPES and 10 mM histidine buffers were prepared by weighing and dissolving the buffer components followed by adjustment of the pH-value at 7.0 using HCl and/or NaOH.

1.2 Methods 1.2.1 Dialysis

Unless otherwise indicated, the trivalent IPV bulk material was dialyzed against 10 mM McIlvaine buffer (pH 7.0) using a 10 kDa molecular weight cut-off, low-binding regenerated cellulose membrane dialysis cassette (Slide-A-Lyzer®, Pierce, Thermo Scientific, Rockford, Ill.) to replace the buffer components of the IPV bulk (M199 medium).

1.2.2 Solutions to be Dried

All excipients were dissolved in McIlvaine buffer at a double concentration of the indicated end concentration. The dialyzed IPV was equally mixed with the formulation to be tested. Subsequently 2 ml glass injection vials (Müller+Müller, Holzminden, Germany) were filled with 0.2 ml of the IPV-excipient mixtures and provided with 13 mm pre-dried (overnight at 90° C.) rubber stoppers (type V9250 from Helvoet Pharma, Alken, Belgium).

1.2.3 Lyophilization and Vacuum-Drying Process

For lyophilization, filled and half-stopped vials were loaded into a Leybold GT4 freeze-dryer or Zirbus pilot/laboratory freeze-drying unit sublimator 2-3-3 at a shelf temperature of −50° C., or at a shelf of 4° C. and then frozen to −50° C. by reducing the temperature at a rate of 1° C./min, which will be denoted as fast and slow freezing, respectively. The vials were kept at a temperature of −50° C. for 2 h. For the primary drying phase the shelf temperature was increased at 0.1° C./min to −45° C., then at 0.02° C./min to −40° C., followed by incubation for 42 h. The secondary drying phase was performed by further increase of the shelf temperature at 0.02° C./min to 10° C., followed by an 8 h during incubation at 10° C. Thereafter, the shelf temperature was increased at 0.02° C./min to 25° C.

For vacuum drying, filled and half-stopped vials were loaded into a Zirbus freeze-drying unit sublimator 2-3-3 at a shelve temperature of 15° C. and kept at that temperature for 10 minutes. The chamber pressure was reduced till 1 mbar in ramping steps of 15 minutes with different rates (1 mbar/min, 0.3 mbar/min, 0.1 mbar/min) and starting at a 25 mbar chamber pressure. The temperature was decreased till −10° C. for 1 h at 0.05 mbar and for 1 h at 0.03 mbar, resulting in no freezing of the formulations (product temperature above eutectic temperature of the formulations). Subsequently, shelf temperature was increased at 0.05° C./min to 30° C. At the end of the cycle, the vials were closed under vacuum, sealed with alu-caps and kept at 4° C. until analysis. An example of the shelf temperatures and chamber pressures during the course of vacuum drying process is shown in Table 1.

TABLE 1

| | $T_{shelf}$ (° C.) | Period (min) | Pressure (mbar) |
|---|---|---|---|
| FT01 | 15 | 10 | — |
| D01 | 15 | 15 | 25 |
| D02 | 15 | 15 | 10 |
| D03 | 15 | 15 | 5 |
| D04 | 15 | 15 | 3 |
| D05 | 15 | 15 | 1 |
| D06 | −10 | 60 | 0.05 |
| D07 | −10 | 60 | 0.03 |
| D08 | −5 | 120 | 0.03 |
| D09 | 5 | 120 | 0.03 |
| D10 | 10 | 120 | 0.03 |
| P01 | 20 | 240 | — |
| P02 | 30 | 240 | — |
| P03 | 4 | 60 | — |

1.2.4 D-Antigen ELISA

Polystyrene 96-well microtiter plates were coated overnight at room temperature with serotype-specific bovine anti-polio serum (RIVM, Bilthoven, The Netherlands). After washing with 0.1% Tween20 in PBS (wash buffer), twofold dilutions of an IPV reference standard and a single dilution of IPV-formulations diluted in assay buffer (PBS with 0.5%

Protifar and 0.1% Tween20) were added (100 μl/well, in duplicate). The plates were incubated at 37° C. for 30 minutes under gentle shaking, extensively washed and a mixture of serotype-specific monoclonal mouse antibodies (mab 3-4-E4 (type 1), 3-14-4 (type 2), 1-12-9 (type 3), all from RIVM, Bilthoven, The Netherlands) and HRP-labeled anti-mouse IgG (GE Healthcare, Buckinghamshire, UK) was added. Subsequently, plates were incubated at 37° C. for 30 minutes under gentle shaking. Plates were washed extensively and ELISA HighLight signal reagent from (Zomerbloemen BV, Zeist, The Netherlands) was added and chemiluminescence was measured during 10-15 minutes by using a luminometer (Berthold Centro LB960).

1.2.5 Moisture-Content Analysis

The water content was determined using a Karl Fischer coulometric titrimeter (Model CA-06 Moisture meter, Mitsubishi). The principle of the water residue determination by Karl Fischer method is based on the fact that iodine and sulphurdioxide only react in the presence of water. The samples were weighted and subsequently reconstituted in the Karl-Fischer reagent, Hydranal Coulomat A (Fluka, Buchs, Switzerland). The reconstituted sample was withdrawn into a syringe and injected into the titration vessel. Each vial was measured in triplicate. The empty vials were weighted and the water content was calculated based on the water content measured by the titrimeter, the weight of the lyophilized product in the vial, the reconstitution volume of the reagent, titration volume and the water content of the blank titration.

1.2.6 Differential Scanning Calorimetry (DSC)

The thermodynamic behaviour of the formulations was determined by differential Scanning calorimetry (DSC), a method which measures the temperatures and heat flow, associated with phase transitions in materials, as a function of time and temperature. The freeze-dried formulations were filled in an aluminium DSC pan and subjected to a controlled temperature program in a differential scanning calorimeter (DSC Q100, TA Instruments). The sample was heated from 0° C. to 150° C. at a heating rate of 20° C./min and the sample chamber was purged with nitrogen gas (50 ml/min). The glass transition temperatures (Tg) were determined as the midpoint of the discontinuities in the heat flow curves using software (Universal Analysis 2000, TA Instruments).

2. Results 2.1 Stabilizing Different IPV Subtypes During Lyophilization

In the first experiment (Experiment A) four well known stabilizing sugars/polyols (sucrose, trehalose, mannitol and dextran), as well as sodium chloride were evaluated for their stabilizing potential (FIG. 1). The study was set up with a design of experiments approach in order to obtain an optimal formulation for lyophilization of IPV.

Different IPV-formulations were lyophilized as described above (section 1.2.3). Lyophilized cakes were reconstituted by adding an equal amount of water as the starting volume and the D-antigen recovery was determined by an ELISA (section 1.2.4). Recoveries were shown as the percentages of the D-antigen content in the liquid formulations, which were measured before lyophilization.

The trivalent IPV formulation, without any additives, IPV 1:1 diluted with McIlvaine buffer, showed recoveries <10% for all serotypes after lyophilization (FIG. 1; A1). Type 2 IPV showed to be the most stable serotype in all formulations with maximum D-antigen recoveries of ±80%. Dextran seemed to have a negative effect on D-antigen recovery of the lyophilized IPV formulations, especially for type 1 and 3. Best results, with maximum recoveries of ±55%, ±85% and ±50% for serotype 1, 2 and 3 respectively, were obtained with formulations containing sucrose and/or trehalose in combination with mannitol (FIG. 1; formulations A3, A4, A12 and A16). Addition of NaCl had no positive effect on the recovery of IPV after lyophilization.

This first pilot experiment clearly shows the complexity of lyophilizing a trivalent polio vaccine in which each IPV serotype prefers its own stabilizing agents. In a formulation with 10% mannitol type 1 and type 3 preferred the presence of high concentrations sucrose without trehalose, whereas type 2 preferred a high concentration of trehalose without sucrose (FIG. 2).

In the next experiment (Experiment B) the stabilizing potential of a mixture of glutamate, a saccharide, and a polymer was investigated. Different combinations of the excipients sucrose, trehalose, monosodium glutamate (MSG), hydroxyethyl starch (HES) and NaCl were investigated. Lyophilization of trivalent IPV with formulations based on MSG together with disaccharide, sucrose and/or trehalose, showed D-antigen recoveries of 50-60%, 70-95% and 50-65% for the three serotypes respectively (FIG. 3; formulations B4, B7, B9, B12, B13). Formulations based on only 8% HES or 63 mM NaCl did not protect IPV during lyophilization (FIG. 3; B5 and B10). The addition of NaCl to a formulation with sucrose showed an 5-10% increase in D-antigen recovery after lyophilization (FIG. 3; B2 and B16).

2.2 Impact of the Drying Process and Formulation

In the next test results are shown of typical formulations used for drying of biopharmaceuticals in relation to the drying process. Formulations containing trivalent IPV were dried by vacuum drying (a drying method without freezing), freeze drying using a fast freezing step (direct placement of the product on pre-cooled shelves of −50° C.) and freeze drying using a slow freezing step (placement of product on shelves of 4° C. and freezing towards −50° C.). As shown in FIG. 4 standard formulations, e.g. based on sucrose or trehalose, partially protect IPV upon vacuum drying. However, these formulations do not give protection upon freeze drying.

2.3 Screening of Excipients

In the next experiment (Experiment C) different formulations containing sorbitol, mannitol, sucrose and/or MSG combined with some amino acids, proteins/peptides or other stabilizing agents were tested (Table 2). In order to investigate the effect of salt in the lyophilized IPV-formulation, the C-formulations were also tested with addition of 125 mM NaCl. No clear effect of the NaCl on the D-antigen recoveries was observed (data not shown). Having a first look on the antigenicity results directly after lyophilization, it was clear that formulation C13, containing 5% sorbitol, 5% peptone and 1% lithium chloride (LiCl), showed the highest recoveries for all serotypes; ±85%, ±100% and ±85% for type 1, 2 and 3 respectively (FIG. 5). Substitution of the LiCl-compound in 1.8% $MgCl_2$ resulted in a decrease of ±5%±20% and 15% in D-antigen recovery for the three serotypes. However, these formulations showed relative high residual moisture contents, 2.1% for the $MgCl_2$-containing formulation and 6.2% for the formulation with LiCl. The addition of a very small amount of surfactant Tween 80 to a formulation containing sucrose, trehalose and the amino acids glycine and lysine increased the D-antigen recoveries with 5-15% (FIG. 5; C8, C9). The formulations based on sorbitol, mannitol and MSG (C2, C3, C4 and C7) showed recoveries of more than 65%, 80% and 70% for type 1, 2 and 3 respectively.

In this study, the combination of sorbitol, peptone and the salts LiCl or MgCl$_2$ seemed to have a positive effect on the D-antigen recovery directly after lyophilization of IPV. Another notable formulation is the mixture of sorbitol, mannitol and MSG, which showed that the presence of polyols in combination with MSG stabilizes the IPV during lyophilization.

Figure 6:
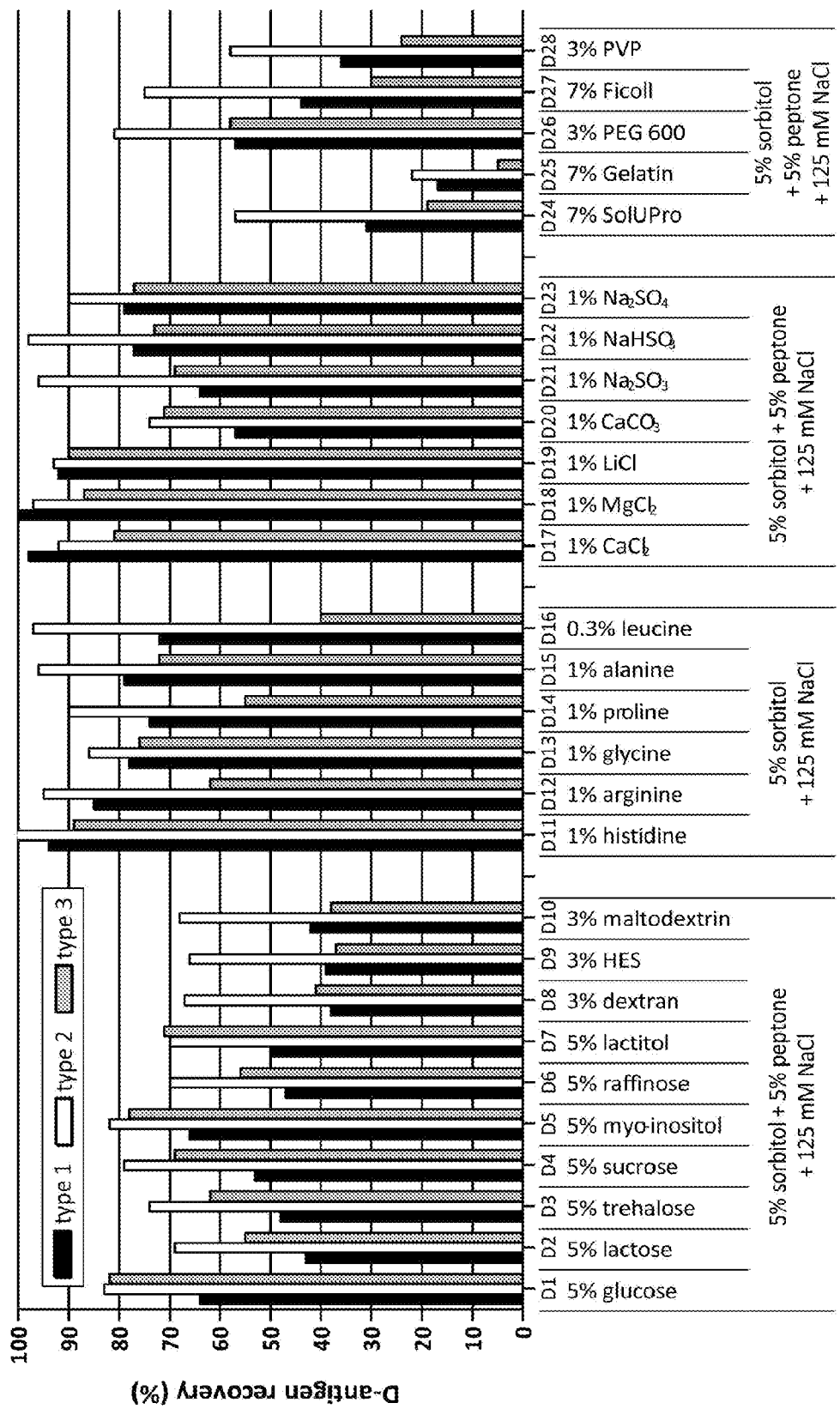
FIG. 6 D-antigen recovery directly after lyophilization of serotype 1, 2 and 3 IPV-formulations (experiment D). All formulations contain 5% sorbitol and 125 mM NaCl and, excluding D11-D16, 5% peptone and are further as indicated.

The glass transition temperature of the lyophilized formulations was measured (Table 2), but showed no clear relation with the D-antigen recoveries. Formulations containing ovalbumine and peptone showed the highest glass transition temperatures.

or other stabilizing agents, like surfactants or proteins. The formulation with sorbitol, NaCl and 1% histidine showed recoveries of 90-100% directly after the freeze-drying process (FIG. 6; D11). As observed earlier, the MgCl$_2$-containing formulation showed auspicious stabilizing capacity during lyophilization, which was similar for the calciumchloride (CaCl$_2$)- and lithium chloride (LiCl)-containing IPV formulations (FIG. 6; D17-19). During the screening phase accelerated stability has been evaluated to select the excipients on their ability to provide a stable lyophilized product as well, even after subsequent storage at high temperature.

TABLE 2

Composition of the lyophilized IPV-formulations (Experiment C). Residual moisture content (RMC) was determined by Karl Fischer and the T$_g$ of the dried cake by DSC.

| | SOR | MAN | SUC | MSG | Sugars/polyols | Amino acids | Proteins | Other | RMC (%) | T$_g$ (° C.) |
|---|---|---|---|---|---|---|---|---|---|---|
| C1 | — | — | — | — | — | — | — | — | 3.6 | n.d. |
| C2 | 7% | 7% | — | 2% | — | 2% Glycine | 7% Ovalbumin | — | 0.3 | 37.2 |
| C3 | 7% | 7% | — | 2% | — | 2% Glycine | 7% Ovalbumin | 1 mM EDTA | n.d. | 38.3 |
| C4 | 7% | 7% | — | 2% | — | 2% Glycine | — | — | 1.9 | 53.5 |
| C5 | — | — | 3% | — | 3% Dextran 3% Myo-Inositol | — | 3% Ovalbumin | — | 1.1 | 54.9 |
| C6 | 5% | 5% | 5% | — | — | 2% Glycine 3% Lysine 3% L-Arg | — | — | 1.0 | 37.1 |
| C7 | 5% | 5% | 5% | 3% | — | 2% Glycine 3% Lysine | — | — | 3.3 | 37.2 |
| C8 | — | — | 5% | — | 5% Trehalose | 3% Lysine 3% Alanine | — | — | 0.5 | 32.3 |
| C9 | — | — | 5% | — | 5% Trehalose | 3% Lysine 3% Alanine | — | 0.01% Tween80 | 0.5 | 34.1 |
| C10 | — | — | 5% | — | — | 3% Lysine 3% Alanine | — | 3% Ca-Lactobionate | 1.0 | 31.2 |
| C11 | — | — | 5% | — | — | 3% Lysine 3% Alanine | 3% Rec. Gelatin | — | 0.3 | 35.7 |
| C12 | 5% | — | — | — | — | — | 5% Peptone | 1.8% MgCl$_2$ | 2.1 | 44.7 |
| C13 | 5% | — | — | — | — | — | 5% Peptone | 1% LiCl | 6.2 | n.d. |
| C14 | — | — | 5% | — | 5% Trehalose | — | 5% Peptone | — | 0.5 | 35.6 |

Figure 7:
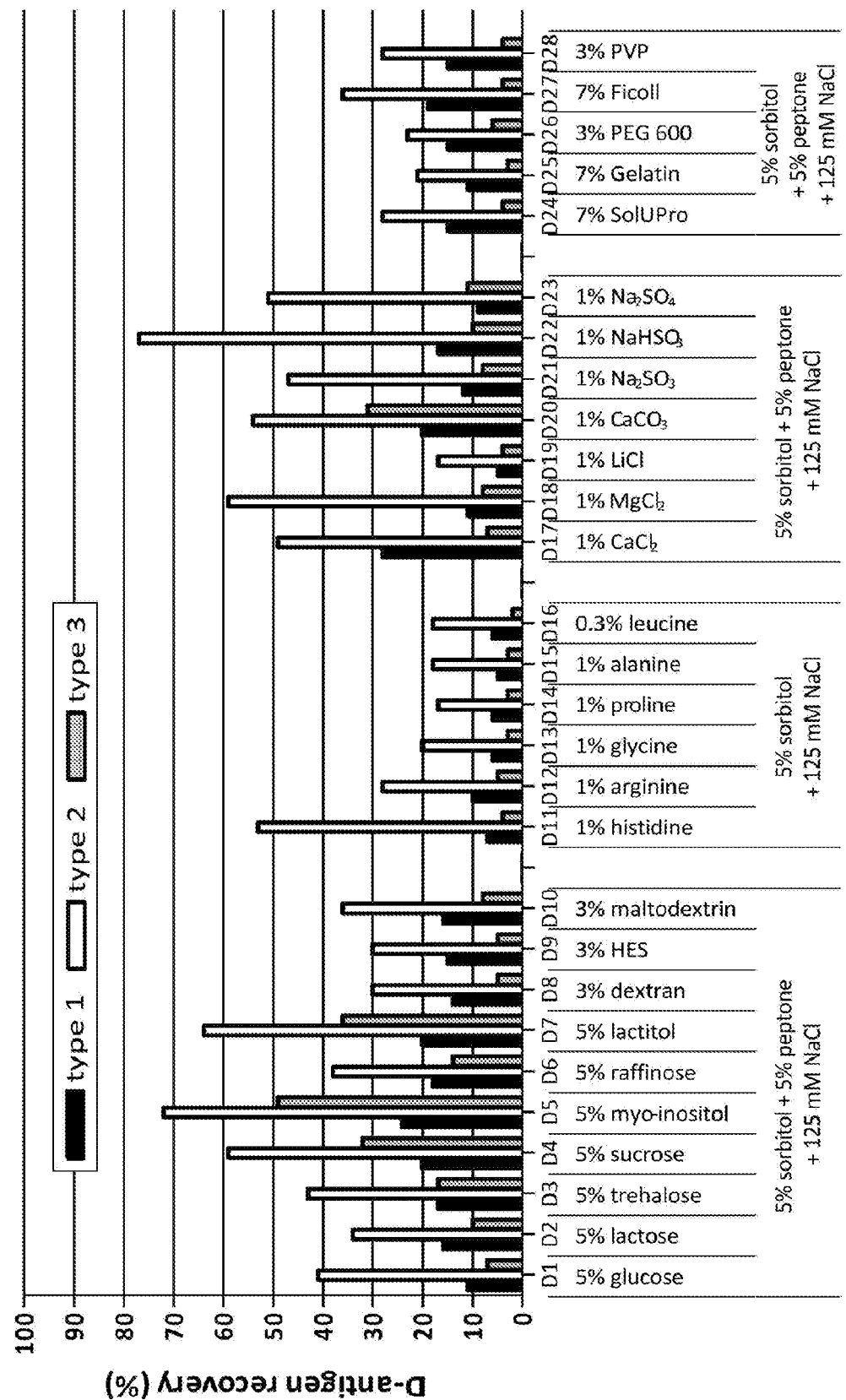
FIG. 7 Accelerated stability testing of lyophilized serotype 1, 2 and 3 IPV-formulations as indicated (experiment D) as determined by D-antigen recovery after one week incubation at 45° C.

Based on these findings a new screening experiment (Experiment D) was designed. Since the most promising recoveries were obtained with formulations based on sorbitol, peptone and Mg or Li-chloride, we designed an experiment based on 10% sorbitol, 5% peptone and 125 mM NaCl. Ovalbumine was discarded since it is from animal origin, thus an undesirable excipient in a vaccine for human use. In order to get more insight in the IPV stabilizing mechanism of several excipients, formulations containing 10% sorbitol, 5% peptone and 125 mM NaCl were combined with either a sugar/polyol, an amino acid (instead of 5% peptone), a salt 2.4 Accelerated Stability Testing Although some formulations showed acceptable D-antigen recoveries directly after lyophilization, after one week incubation at 45° C. the D-antigen recoveries of these four formulations were dropped till percentages below 30%, 60% and 10% for respectively serotype 1, 2 and 3 (FIG. 7). The formulation with 5% myo-inositol represented the highest recoveries after incubation at 45° C., but still a decrease of ±40%, 10% and 30% was observed for the three serotypes, which showed again IPV type 2 to be the most stable serotype (FIG. 7; D5). Upon one week storage at 45° C., the formulation containing 1% lactitol showed less than 10% decrease in D-antigen recovery for serotype 2, unfortunately serotype 1 and 3 showed a decrease of >30% (FIG. 7; D7).

In order to further investigate the combination with sorbitol, mannitol, MSG and the stabilizing potential of peptone and MgCl$_2$, a new design of experimental set up was performed to determine the relationship between the different excipients and D-antigen recovery after lyophilization. The following variables were included in Experiment E: 0/10% sorbitol, 0/10% sucrose, 0/10% mannitol, 0/10% MSG, 0/5% peptone and/or 0/5% MgCl$_2$ and freezing speed was investigated in this experiment. Slow freezing means that the vials were placed on shelves at 4° C. and subsequently cooled till −50° C. at a rate of 0.1° C./min, where fast freezing means that the vials were directly placed at shelves pre-cooled at −50° C. The results are shown in FIG. 8A for the fast freezing rate and in FIG. 8B for the slow freezing rate.

Figure 8A:
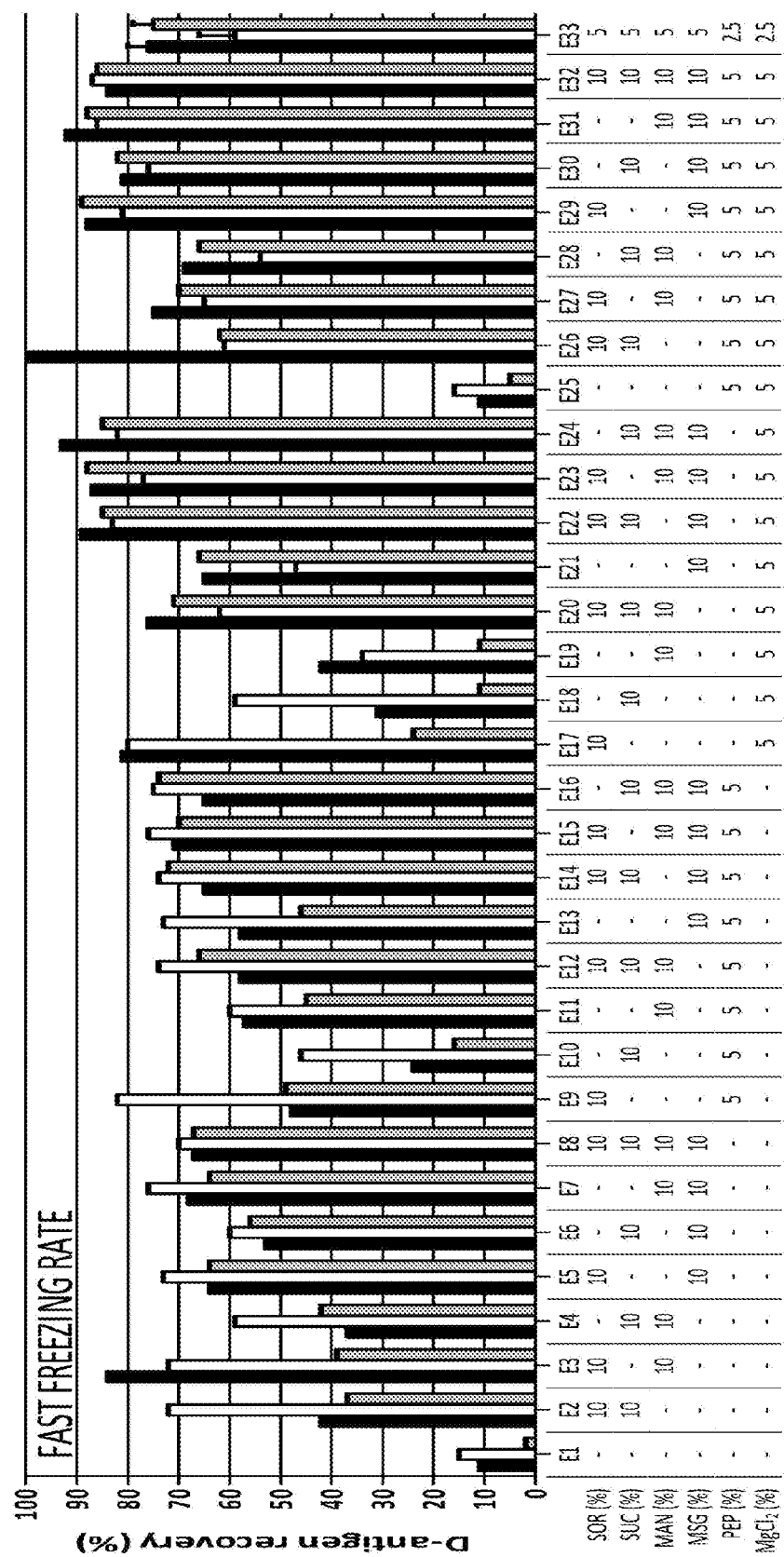
FIG. 8 D-antigen recovery directly after lyophilization of serotype 1, 2 and 3 IPV-formulations as indicated (experiment E). The stabilizing effects of sorbitol (SOR), sucrose (SUC), mannitol (MAN), mono-sodium glutamate (MSG), peptone (PEP) and $MgCl_2$ were tested by using fast (panel A) and slow (panel B) freezing rates.
Figure 8B:
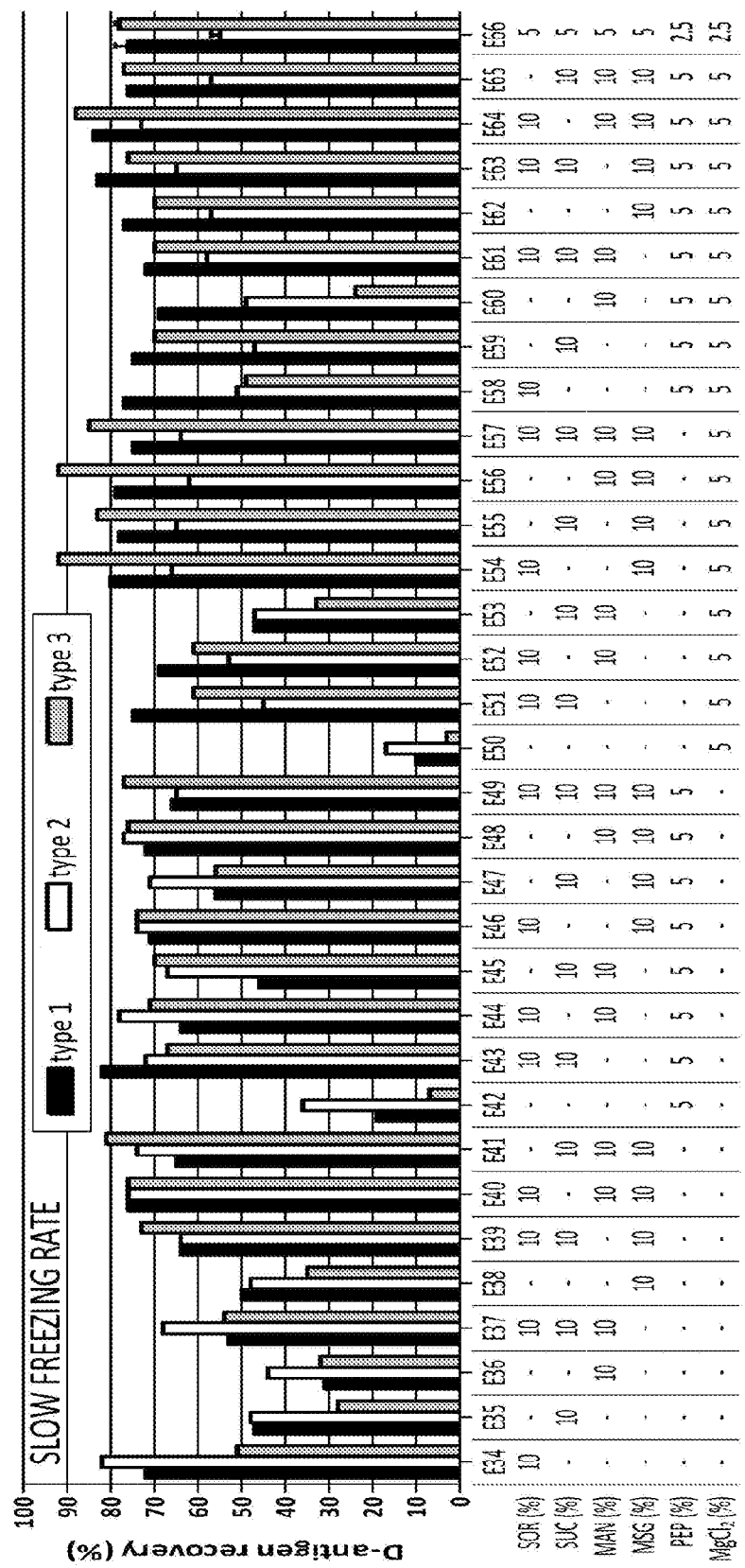
Figure 9A:
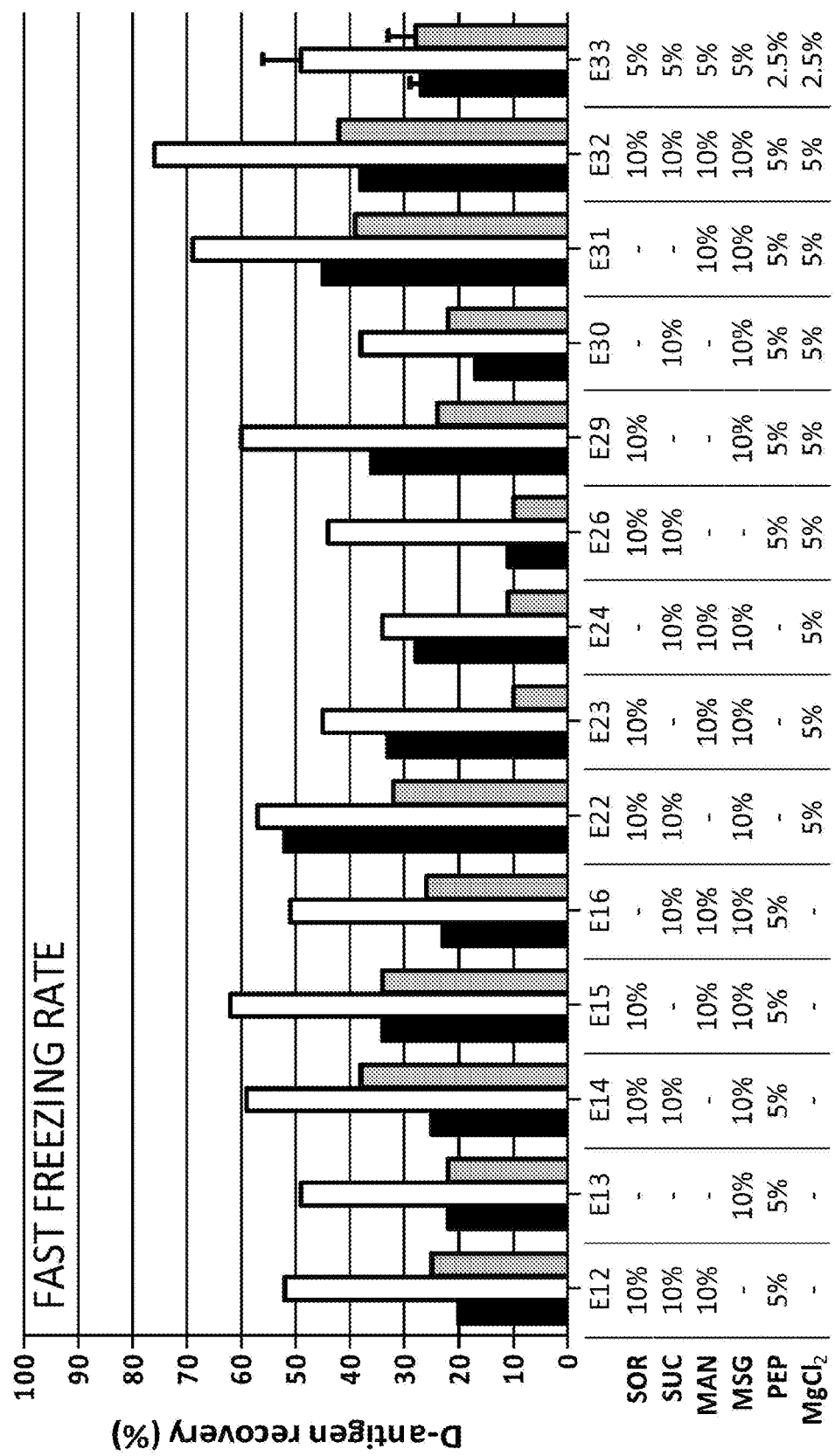
FIG. 9 Stability of lyophilized serotype 1, 2 and 3 IPV-formulations as indicated (experiment E) after one week incubation at 45° C. and using fast (panel A) and slow (panel B) freezing rates. Only the most promising formulations directly after lyophilization are shown.

Having a first look on the D-antigen recoveries after lyophilization, the fast frozen formulations containing MSG and MgCl$_2$ in combination with a sugar/polyol showed the highest recoveries of ±80-90% for all serotypes (FIG. 8A; E22-24, E29-32). For the slow frozen samples the MgCl$_2$-containing formulations showed recoveries of 75-90% for type 1 and 3 (FIG. 8B; E54-57, E63-66). However, for serotype 2 only formulations of the sugar(s) in combination with peptone showed recoveries of ±70% (FIG. 8B, E43-48). To have an indication of the reproducibility of the experiment formulation H33 and H66 were tested in triplicate and showed standard deviations <10% for all serotypes. From the comparison of the D-antigen recoveries of these two formulations, directly after lyophilization (FIG. 8) or after one week incubation at 45° C. (FIG. 9), it is clear that freezing rate did not influence the recovery significantly for these IPV formulations.

Experiment E was set up on the basis of 'Design of Experiment' using the "Modde" software from Umetrics. Besides recovery of D-antigen after lyophilization, also recoveries after lyophilization and subsequent storage at 37° C. or 45° C. were used as output in the design. The output as function of the formulations was modulated and put in a model using Modde. This revealed which formulation parameters affected the recovery after lyophilization and storage (data not shown).

The most important formulation parameters for each of the viral subtypes are summarized in Tables 3-5.

TABLE 3

| | Recovery of D-antigen of type 1 | | |
|---|---|---|---|
| formulation parameter | after lyophilization % | after storage at 37° C. % | after storage at 45° C. % |
| MSG | 9 | 10 | 7 |
| Sorbitol | 8 | 6 | 4 |
| MgCl$_2$ | 7 | 6 | 3 |
| Peptone | | 6 | 4 |
| Mannitol | 4 | 6 | |
| MSG* MgCl$_2$ | | | 4 |

TABLE 4

| | Recovery of D-antigen of type 2 | | |
|---|---|---|---|
| formulation parameter | after lyophilization % | after storage at 37° C. % | after storage at 45° C. % |
| MSG | 7 | 9 | 9 |
| Sorbitol | 7 | 7 | 5 |
| MgCl$_2$ | | | |
| Peptone | | 10 | 10 |
| Mannitol | 3 | 4 | 4 |
| Sucrose | | | 2 |

TABLE 5

| | Recovery of D-antigen of type 3 | | |
|---|---|---|---|
| formulation parameter | after lyophilization % | after storage at 37° C. % | after storage at 45° C. % |
| MSG | 14 | 10 | 10 |
| Sorbitol | 8 | 7 | 7 |
| MgCl$_2$ | 4 | 4 | 4 |
| Peptone | 4 | 12 | 12 |
| Mannitol | 6 | 5 | 5 |
| Sucrose | 4 | 1 | 1 |
| MSG* MgCl$_2$ | | 5 | 5 |

2.5 Substitution of Peptone

Figure 10:
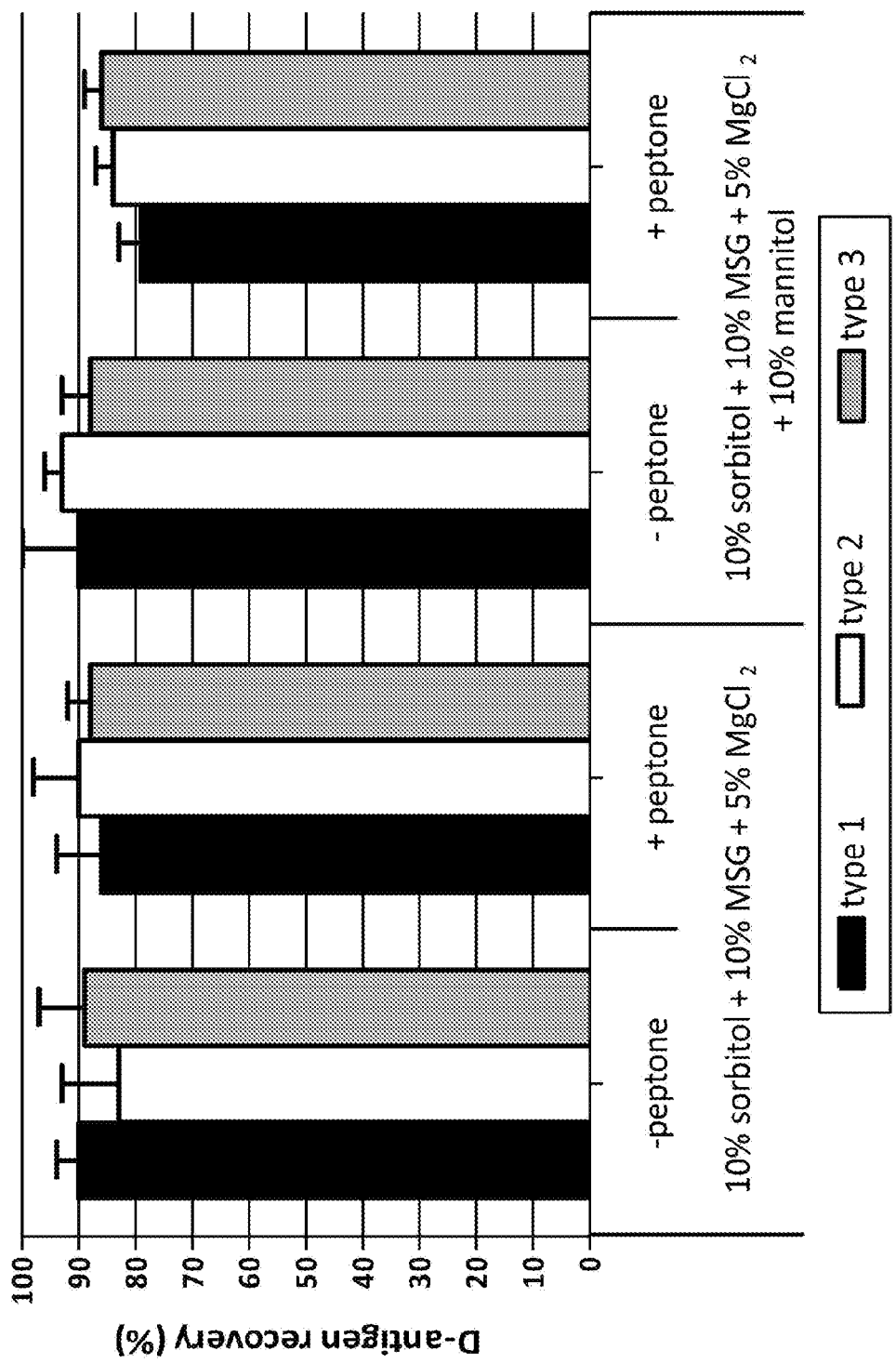
FIG. 10 D-antigen recovery directly after lyophilization of serotype 1, 2 and 3 IPV-formulations (experiment F, n=3). The stabilizing effect of peptone was investigated in an IPV-formulation containing 10% sorbitol, 10% MSG and 5% $MgCl_2$ with or without 10% mannitol. All formulations were fast frozen prior to the drying phase of the lyophilization process.

Since peptone seemed to stabilize the lyophilized IPV during the subsequent storage at a temperature of 45° C., we performed an experiment to investigate the role of peptone in a formulation with 10% sorbitol, 5% MSG and 5% MgCl$_2$ and the same formulation combined with 10% mannitol. No significant differences were found with the addition of 10% mannitol to the formulation containing sorbitol, MSG and MgCl$_2$. Adding 5% peptone did not affected the antigenicity of both formulations (FIG. 10).

Figure 11:
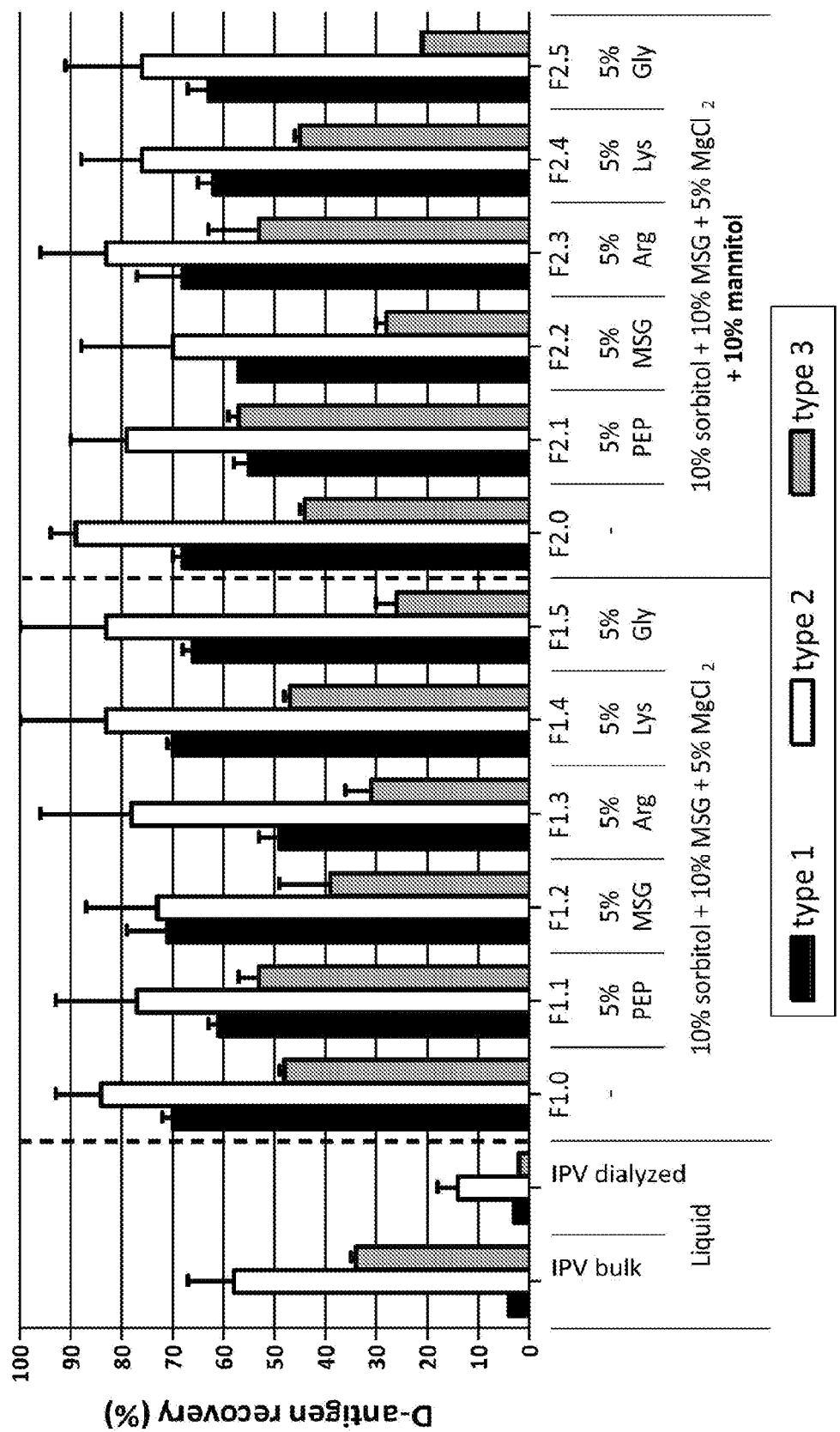
FIG. 11 Stability of lyophilized serotype 1, 2 and 3 IPV-formulations (experiment F, n=3) after one week incubation at 45° C. This experiment investigates whether it is possible to improve the IPV-formulation containing 10% sorbitol, 10% MSG and 5% $MgCl_2$ with or without 10% mannitol during accelerated stability with the addition of peptone or single amino acids.

To find out whether the addition of single amino acids could take over the stabilizing role of peptone during subsequent storage of the lyophilized IPV, amino acids were added to the formulation containing sorbitol, MSG and MgCl$_2$ with or without mannitol. After a week incubation at 45° C. neither peptone or one of the added amino acids showed improved stability of the D-antigen recovery when compared to the control formulation, which contain 10% sorbitol, 10% MSG and 5% MgCl$_2$ (FIG. 11, F1.0-F1.5). In the presence of mannitol the stabilizing capacity of peptone was only shown for type 3, whereas the D-antigen recovery was improved with ±15% when compared to the control sample. However, a significant decreased recovery (p<0.001) was found for type 1 and, even though not significant, type 2 showed also a ±10% lower recovery (FIG. 11; F2.0, F2.1). For all formulations containing sorbitol, MSG and MgCl$_2$ a decrease of ±10% of D-antigen content type 2 was shown after one week 45° C., where the addition of mannitol was found to be stable for type 2 during accelerated stability. Arginine seemed to have stabilizing potential in a formulation (FIG. 11, F2.3) with sorbitol, MSG, MgCl$_2$ and mannitol and showed only ±15% and ±30% decrease in D-antigen recovery for type 1 and 3 respectively after incubation at 45° C. This was comparable to the stabilization by almost the same formulation with peptone instead of arginine (FIG. 11, F2.1).

Due to the fact that an undefined excipient, such as peptone, is not preferred in a human vaccine, a possible substitute for peptone, which could stabilize the IPV during storage, was investigated. Analysis by mass spectrometry and HPLC showed the most abundant amino acids present in peptone (data not shown). The addition of several single amino acids to the formulation containing sorbitol, MSG and MgCl$_2$ did not improve the stability at 45° C. when compared to the control formulation. Where peptone seemed to stabilize serotype 3 in the formulation containing sorbitol, MSG, MgCl$_2$ and mannitol, arginine is able to improve the stability of both serotype 1 and 3. Serotype 2 showed already in the control formulation full maintenance of D-antigen recovery during accelerated stability. Although the exact composition of peptone is hard to determine, the amino acid quantification by reverse-phase HPLC with non-hydrolyzed versus chemical hydrolyzed peptone showed that peptone consists of both single amino acids and peptides, however >90% w/w of the peptone remains undefined. Since peptone seemed to increase glass transition temperature of the studied IPV-formulations, it might be possible to replace the peptone by an excipient with high $T_g$, like sucrose or trehalose.

TABLE 7

Glass transition temperatures (Tg' and Tg) of IPV-formulations containing sorbitol, MSG and MgCl$_2$ with/without mannitol were determined by DSC. The effect of peptone on the glass transition of these formulations was investigated. Single measurements were shown.

| | 10% sorbitol + 10% MSG + 5% MgCl$_2$ | | 10% sorbitol + 10% MSG + 5% MgCl$_2$ + 10% mannitol | |
|---|---|---|---|---|
| | $T_g'$ (° C.) | $T_g$ (° C.) | $T_g'$ (° C.) | $T_g$ (° C.) |
| Control | −47.9 | 35.2 | −44.4 | 38.8 |
| +5% peptone | −44.1 | 39.8 | −42.8 | 48.7 |

The previous experiment did not yielded a worthy substitute for peptone and showed that the formulations with sorbitol, MSG, MgCl$_2$ with or without mannitol gave the best results, even after accelerated stability tests. During this study all formulations were prepared with McIlvaine buffer, which is known to be a suitable buffer for lyophilization of IPV [52]. In order to further optimize the formulation a buffer screening was performed with buffers that are frequently used for lyophilization of biopharmaceuticals [18]. IPV batches in each buffer were prepared by dialysis and non-dialyzed IPV acted as control.

Figure 12B:
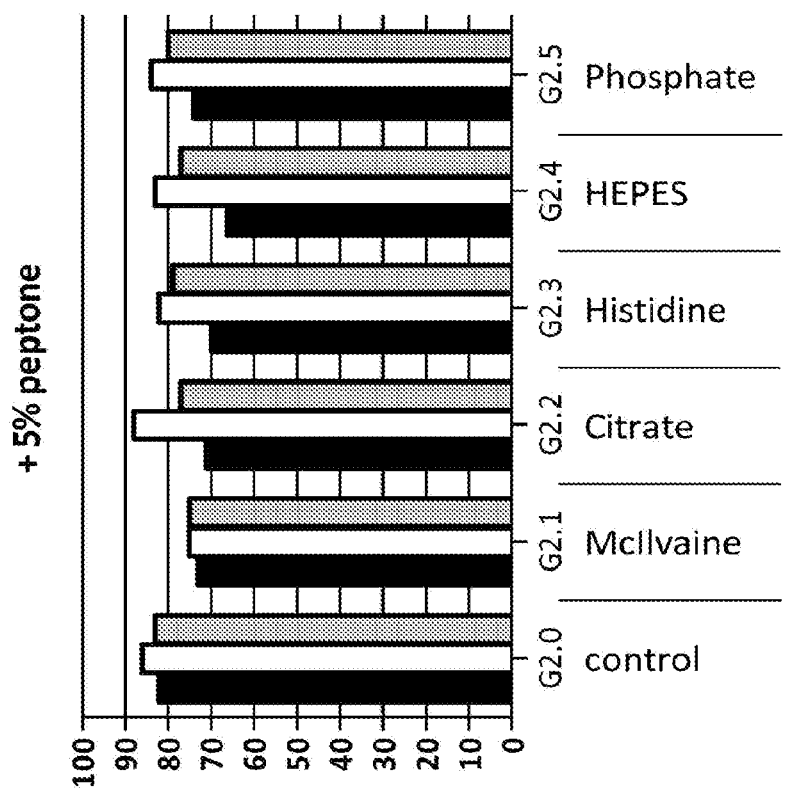
FIG. 12 D-antigen recovery directly after lyophilization of serotype 1, 2 and 3 IPV-formulations with different buffer components as indicated (experiment G). Four formulations as indicated in panels A, B, C and D, all containing 10% sorbitol, 10% MSG and were tested with 10 mM McIlvaine, 10 mM citrate, 10 mM histidine, 10 mM HEPES and 10 mM phosphate buffer. The control formulation was not dialyzed.
Figure 12A:
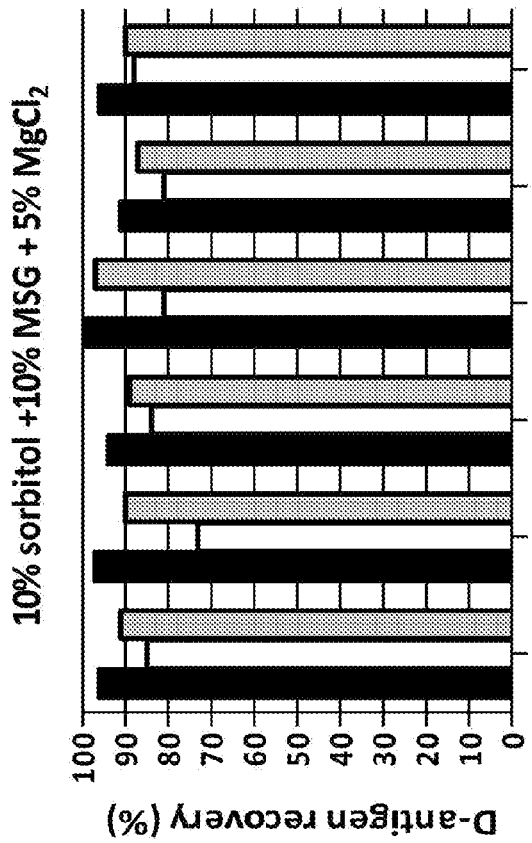

The formulation with sorbitol, MSG and MgCl$_2$ showed recoveries of ±95%, ±85% and ±90% for the three serotypes directly after lyophilization (FIG. 12A; G1.0-G1.5). After addition of peptone the type 1 and 3 D-antigen recoveries were dropped with 10-15%, where type 2 showed similar recoveries when compared to the formulation without peptone (FIG. 12B). McIlvaine buffer showed 10-15% lower recoveries for serotype 2 in comparison with the other buffer components. Histidine buffer seemed to increase the D antigen yield of IPV after lyophilization the IPV-formulation with sorbitol, MSG and MgCl$_2$ (recoveries of >95% for type 1 and 3; FIG. 12A, G1.3). After lyophilization, a D-antigen recovery of 88% for type 2 was reached with the phosphate buffer, where the McIlvaine buffer showed 73% recovery for type 2 (FIG. 12A, G1.5).

Figures 12C, 12D:
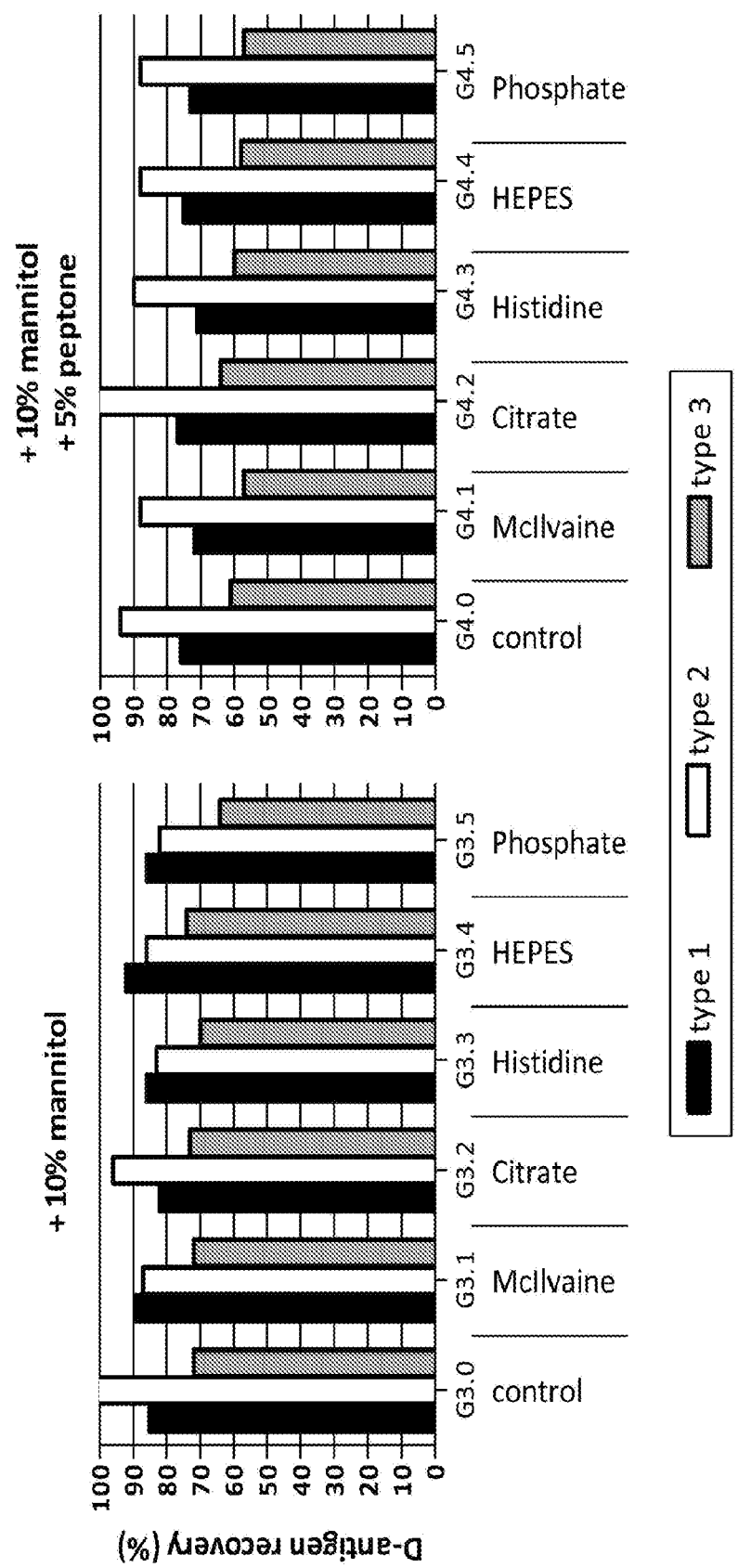

The addition of mannitol to the formulations of sorbitol, MSG, MgCl$_2$. without peptone revealed that serotype 2 prefers the presence of mannitol in the formulation during lyophilization, since recoveries of 85-100% for type 2 were found (FIG. 12C). For type 1 recoveries of 80-90% and for type 3±80% were found for the sorbitol, MSG, MgCl$_2$ and mannitol containing IPV-formulations. The addition of peptone showed ±10% reduction in recovery of type 1 and 3 and similar D-antigen contents for type 2 after lyophilization (FIG. 12D).

2.6 The Effect of Buffer Components

Figure 13A:
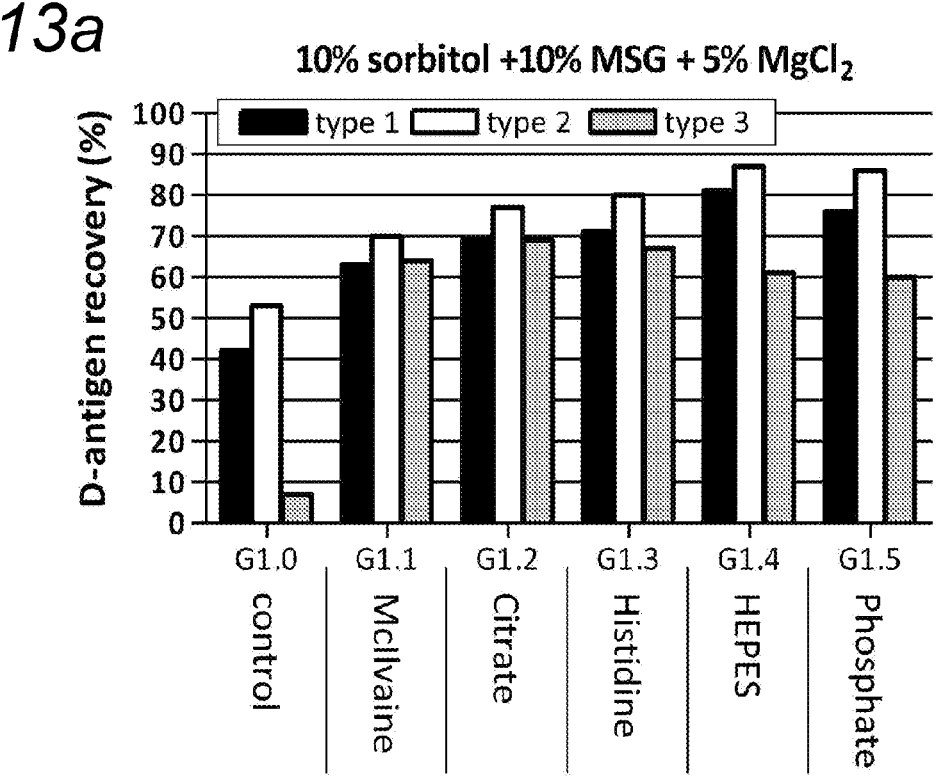
FIG. 13 Stability of lyophilized serotype 1, 2 and 3 IPV-formulations with different buffer components as indicated (experiment G) after lyophilization and subsequent storage at 45° C. for one week. Four formulations, containing 10% sorbitol, 10% MSG and $MgCl_2$ without or with mannitol and without or with peptone were tested in combination with a 10 mM McIlvaine, 10 mM citrate, 10 mM histidine, 10 mM HEPES and 10 mM phosphate buffers. The control formulations were not dialyzed and 1:1 diluted with McIlvaine buffer containing the excipients as indicated.
Figure 13B:
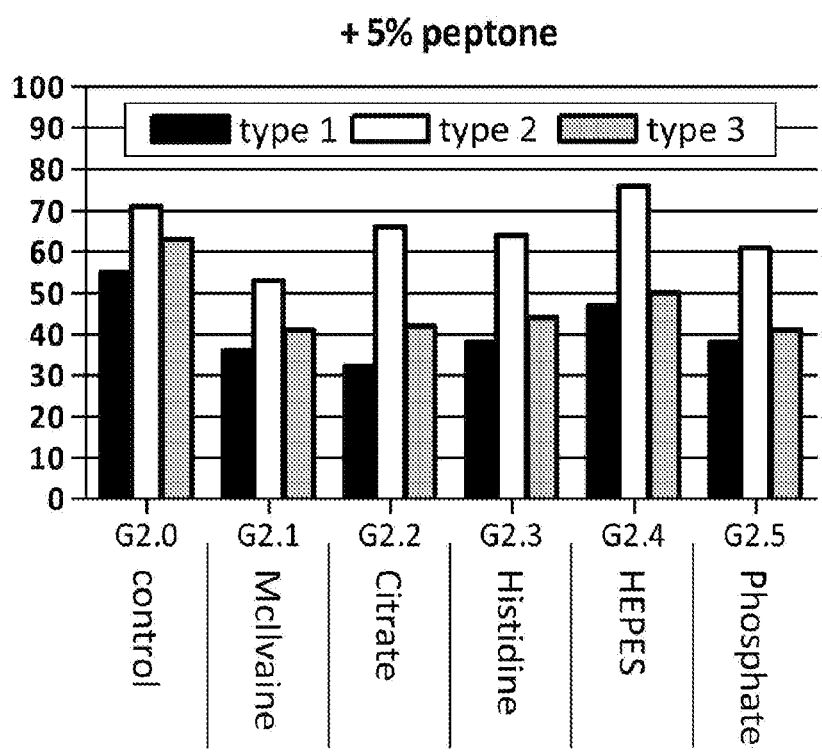
Figure 13C:
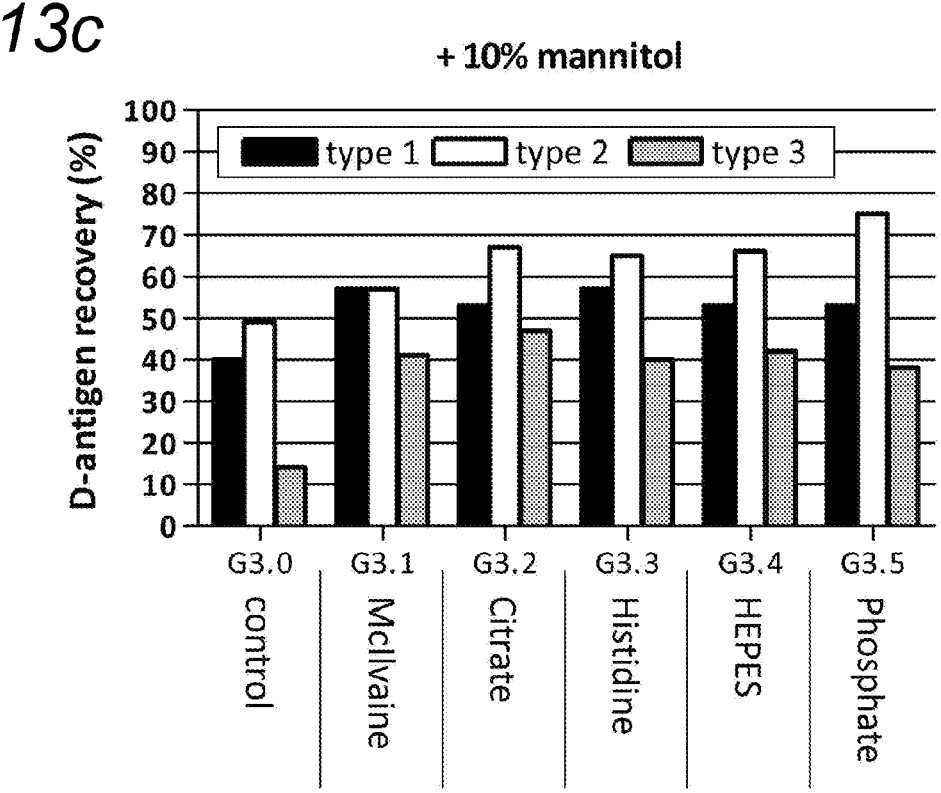
Figure 13D:
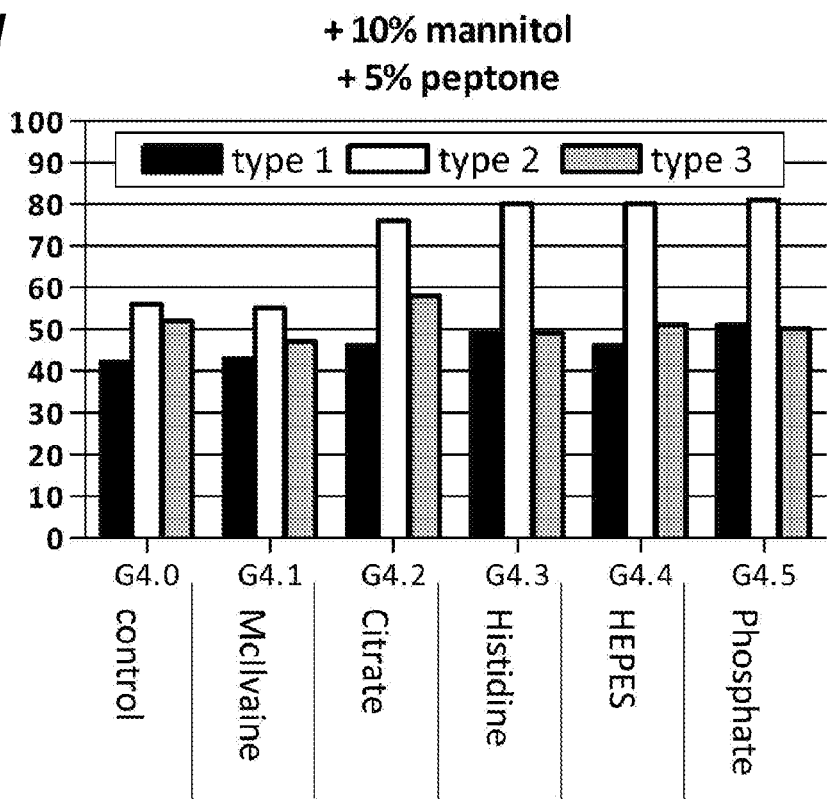

An accelerated stability experiment showed formulation-dependent differences between the used buffers. Whereas the control formulations showed high recoveries directly after lyophilization, recoveries of ±40%, ±50% and <15% for serotype 1, 2 and 3, respectively, were found for the peptone-lacking control formulations after one week incubation at 45° C. (FIG. 13; G1.0 and G3.0). For the control formulations, peptone showed clear improvement of stability of type 1 and 2 when where type 3 showed a decrease of ±25% and ±15% in D-antigen recovery, instead of >90% and 80%, respectively for the formulations without and with mannitol after storage at 45° C. (FIG. 13; G2.0 and G4.0). For the formulation containing sorbitol, MSG and MgCl$_2$ the highest recoveries were observed with HEPES buffer, D-antigen contents of ±80%, ±85% and ±60% for the three serotypes after lyophilization and storage. This means that only 10%, 0% and ±30% reduction in D-antigen recovery occurred during accelerated stability testing for type 1, 2 and 3 respectively. Only for type 3 a better result was observed with citrate buffer; a reduction of ±20% and remained recovery of 79% (FIG. 13A; G1.2). Addition of peptone showed overall 15-25% lower recoveries for all serotype when compared to the same formulation and buffer without peptone (FIG. 13A). Obvious improved stability was shown with the addition of peptone to the formulation with sorbitol, MSG, MgCl$_2$ and mannitol. Where the different buffer formulations without peptone showed maximum recoveries of ±55%, ±75% and ±45%, the same buffers with peptone showed recoveries of ±50%, ±80% and ±55% (FIG. 13B). The formulation based on phosphate buffer with the excipients sorbitol, MSG, MgCl$_2$, mannitol and peptone showed to be the most stable formulation with reduced recoveries of ±30% for type 1 and only ±10% for type 2 and 3 after incubation at 45° C.

2.7 Formulations Suitable for Stabilization Independent of Drying Method

Figure 14:
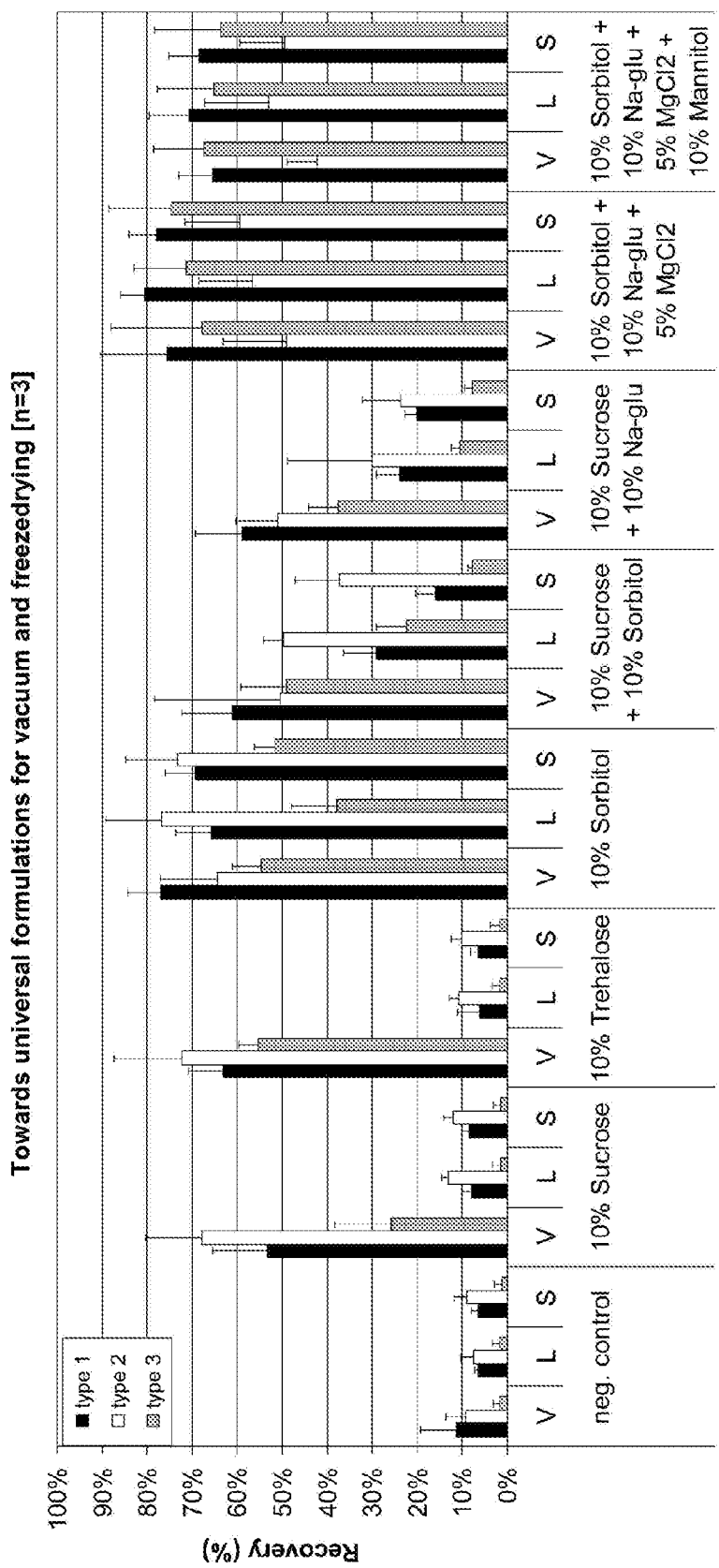
FIG. 14 D-Antigen recovery directly after vacuum drying (V), lyophilization with a slow freezing rate (L) and lyophilization with a fast freezing rate (S). The stabilizing effect of different formulations compared to IPV vaccine without addition of stabilizers (negative control) and sucrose or trehalose formulated IPV.
Figure 15:
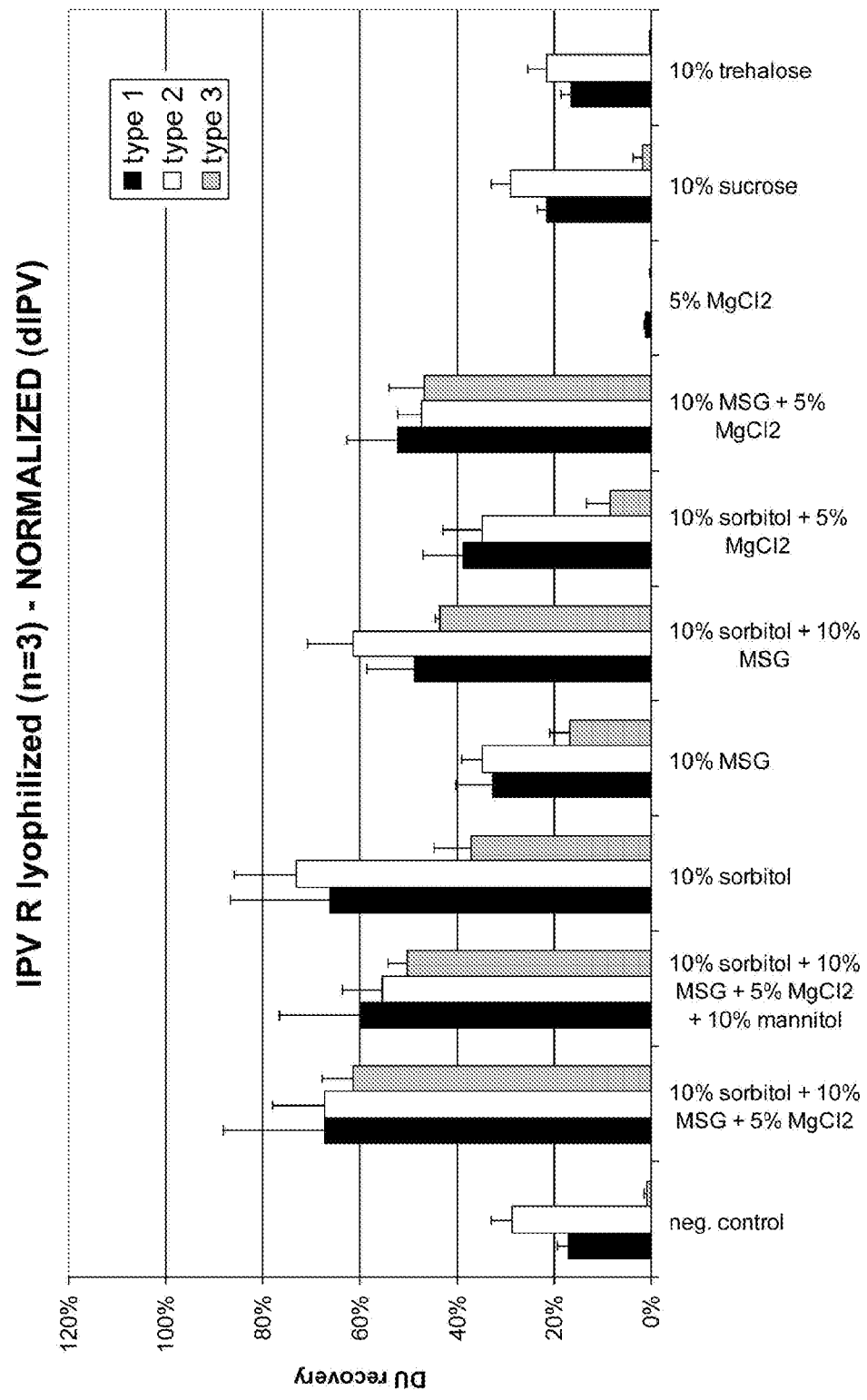
FIG. 15 D-antigen recovery directly after lyophilization of serotype 1, 2 and 3 IPV-formulations as indicated.
Figure 16:
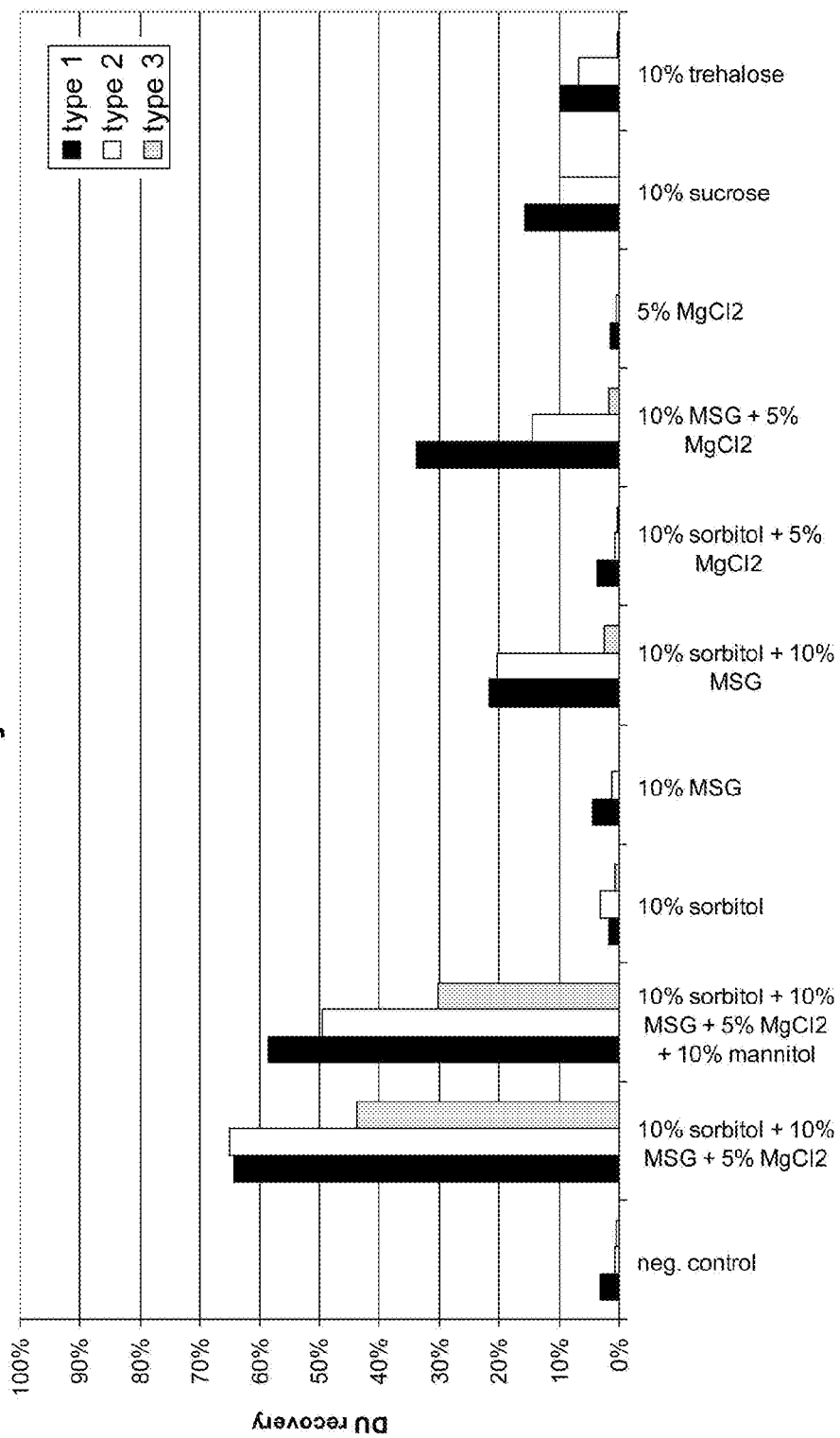
FIG. 16 Stability of serotype 1, 2 and 3 IPV-formulations as indicated after lyophilization and subsequent storage at 45° C. for one week, as determined by D-Antigen recovery.

FIG. 14 shows that only formulations containing sorbitol can resist stresses caused by the different drying methods. This could further be improved by inclusion of MSG and MgCl$_2$ (especially type 3), resulting in formulations that gave comparable or even higher recoveries than vacuum drying with trehalose or sucrose. From earlier results (Experiment E) we concluded that the formulations based on sorbitol, MSG and $MgCl_2$ possesses the best recovery after accelerated stability testing.

2.8 Formulations without Peptone

One of the better formulation without peptone that we found in above experiments, is a formulation containing 10% sorbitol+10% MSG+5% $MgCl_2$. In an additional experiment we evaluated what the impact was of the primary excipients in this formulation. The results were compared with 2 standard formulations based on sucrose and trehalose. The results direct after lyophilization are shown in the FIG. 15. From FIG. 15 we conclude that primarily sorbitol is responsible for recovery of IPV after lyophilization, especially for subtypes 1 and 2. The combination of MSG and $MgCl_2$ shows significant stabilization of the three IPV subtypes. Compared to sorbitol only, the combination of sorbitol, MSG and $MgCl_2$, showed the best recoveries after lyophilization, especially for type 3.

Upon accelerated stability evaluation as shown in FIG. 16, most of the formulations showed an enormous decrease in recovery, also the formulation containing only sorbitol.

However, the formulations containing 10% sorbitol+10% MSG+5% MgCl$_2$ (with/without mannitol) showed high recoveries after storage at 45° C. for one week.

REFERENCES

1. Bonnet, M. C. and A. Dutta, World wide experience with inactivated poliovirus vaccine. Vaccine, 2008. 26 (4978): p. 4983.
2. Minor, P., Vaccine-derived poliovirus (VDPV): Impact on poliomyelitis eradication. Vaccine, 2009. 27 (20): p. 2649-2652.
3. Shahzad, A. and G. Köhler, Inactivated Polio Vaccine (IPV): A strong candidate vaccine for achieving global polio eradication program. Vaccine, 2009. 27: p. 5293-5294.
4. Ehrenfeld, E., J. Modlin, and K. Chumakov, Future of polio vaccines. Expert Rev Vaccines, 2009. 8 (7): p. 899-905.
5. John, J., Role of injectable and oral polio vaccines in polio eradication. Expert Rev Vaccines, 2009. 8 (1): p. 5-8.
6. Westdijk, J., et al., Characterization and standardization of Sabin based inactivated polio vaccine: proposal for a new antigen unit for inactivated polio vaccines. Vaccine, 2011. 29 (18): p. 3390-7.
7. Clements, C. J., G. Larsen, and L. Jodar, Technologies that make administration of vaccines safer. Vaccine, 2004. 22 (15-16): p. 2054-2058.
8. Friede, M. and M. T. Aguado, Need for new vaccine formulations and potential of particulate antigen and DNA delivery systems. Adv Drug Deliv Rev, 2005. 57 (3): p. 325-331.
9. Moynihan, M. and I. Petersen, The durability of inactivated poliovirus vaccine: studies on the stability of potency in vivo and in vitro. J Biol Stand, 1982. 10 (3): p. 261-8.
10. WHO, Temperature sensitivity of vaccines. 2006.
11. Sawyer, L. A., et al., Deleterious effect of thimerosal on the potency of inactivated poliovirus vaccine. Vaccine, 1994. 12 (9): p. 851-6.
12. Vidor, The place of DTP/eIPV vaccine in routine paediatric vaccination. Rev Med Virol, 1994. 4: p. 261-77.
13. Bruce Aylward, R., et al., Risk management in a polio-free world. Risk Anal, 2006. 26 (6): p. 1441-8.
14. Sutter, R. W., V. M. Caceres, and P. Mas Lago, The role of routine polio immunization in the post-certification era. Bull World Health Organ, 2004. 82 (1): p. 31-9.
15. Thompson, K. M. and R. J. Duintjer Tebbens, The case for cooperation in managing and maintaining the end of poliomyelitis: stockpile needs and coordinated OPV cessation. Medscape J Med, 2008. 10 (8): p. 190.
16. Tebbens, R. J., et al., Optimal vaccine stockpile design for an eradicated disease: application to polio. Vaccine, 2010. 28 (26): p. 4312-27.
17. Amorij, J. P., et al., Development of stable influenza vaccine powder formulations: challenges and possibilities. Pharm Res, 2008. 25 (6): p. 1256-73.
18. Wang, W., Lyophilization and development of solid protein pharmaceuticals. Int J of Pharm, 2000. 203: p. 1-60.
19. Chang, L. and M. J. Pikal, Mechanisms of protein stabilization in the solid state. J of Pharm Sc, 2009. 98 (9): p. 2886-2908.
20. Arakawa, T., et al., Factors affecting short-term and long-term stabilities of proteins. Adv Drug Deliv Rev, 2001. 46 (1-3): p. 307-26.
21. Bhatnagar, B. S., R. H. Bogner, and M. J. Pikal, Protein stability during freezing: separation of stresses and mechanisms of protein stabilization. Pharm Dev Technol, 2007. 12 (5): p. 505-23.
22. Skrabanja, A. T., et al., Lyophilization of biotechnology products. PDA J Pharm Sci Technol, 1994. 48 (6): p. 311-7.
23. Dias, C. L., et al., The hydrophobic effect and its role in cold denaturation. Cryobiology, 2010. 60 (1): p. 91-9.
24. Carpenter, J. F. and J. H. Crowe, The mechanism of cryoprotection of proteins by solutes. Cryobiology, 1988. 25 (3): p. 244-55.
25. Chang, B. S., B. S. Kendrick, and J. F. Carpenter, Surface-induced denaturation of proteins during freezing and its inhibition by surfactants. J Pharm Sci, 1996. 85: p. 1325-1330.
26. Tang, X. C. and M. J. Pikal, Measurement of the kinetics of protein unfolding in viscous systems and implications for protein stability in freeze-drying. Pharm Res, 2005. 22 (7): p. 1176-85.
27. Webb, S. D., et al., A new mechanism for decreasing aggregation of recombinant human interferon-gamma by a surfactant: Slowed dissolution of lyophilized formulations in a solution containing 0.03% polysorbate 20. J Pharm Sci, 2002. 91: p. 543-558.
28. Rupley, J. A. and G. Careri, Protein hydration and function. Adv Protein Chem, 1991. 41: p. 37-172.
29. Carpenter, J. F., T. Arakawa, and J. H. Crowe, Interactions of stabilizing additives with proteins during freeze-thawing and freeze-drying. Dev Biol Stand, 1992. 74: p. 225-38; discussion 238-9.
30. Carpenter, J. F. and J. H. Crowe, An infrared spectroscopic study of the interactions of carbohydrates with dried proteins. Biochemistry, 1989. 28 (9): p. 3916-22.
31. Tian, F., S. Sane, and J. H. Rytting, calorimetric investigation of protein/amino acid interactions in the solid state. Int J Pharm, 2006. 310: p. 175-186.
32. Akers, M. J., et al., Glycine crystallization during freezing: the effects of salt form, pH, and ionic strength. Pharm Res, 1995. 12 (10): p. 1457-61.
33. Mattern, M., et al., Formulation of proteins in vacuum-dried glasses. II. Process and storage stability in sugar-free amino acid systems. Pharm Dev Technol, 1999. 4 (2): p. 199-208.
34. Costantino, H. R., et al., Deterioration of lyophilized pharmaceutical proteins. Biochemistry (Mosc), 1998. 63 (3): p. 357-63.
35. Kadoya, S., et al., Freeze-drying of proteins with glass-forming oligosaccharide-derived sugar alcohols. Int J Pharm, 2010. 389 (1-2): p. 107-13.
36. Li, S., et al., Effects of reducing sugars on the chemical stability of human relaxin in the lyophilized state. J Pharm Sci, 1996. 85 (8): p. 873-7.
37. Franks, F., Long-term stabilization of biologicals. Biotechnology (N Y), 1994. 12 (3): p. 253-6.
38. Yu, L., et al., Existence of a mannitol hydrate during freeze-drying and practical implications. J Pharm Sci, 1999. 88 (2): p. 196-8.
39. Hancock, B. C. and G. Zografi, Characteristics and significance of the amorphous state in pharmaceutical systems. J Pharm Sci, 1997. 86 (1): p. 1-12.
40. Schmitt, E. A., D. Law, and G. G. Zhang, Nucleation and crystallization kinetics of hydrated amorphous lactose above the glass transition temperature. J Pharm Sci, 1999. 88 (3): p. 291-6.
41. Fox, K. C., Biopreservation. Putting proteins under glass. Science, 1995. 267 (5206): p. 1922-3.

42. Crowe, J. H., J. F. Carpenter, and L. M. Crowe, The role of vitrification in anhydrobiosis. Annu Rev Physiol, 1998. 60: p. 73-103.
43. van Ingen, C. and C. S. Tan, Preservation mixture and use thereof, W.I.P. Organization, Editor. 2010, De Staat Der Nederlanden, vert. door de minister van VWS.
44. Bam, N. B., et al., Tween protects recombinant human growth hormone against agitation-induced damage via hydrophobic interactions. J Pharm Sci, 1998. 87 (12): p. 1554-9.
45. Christensen, D., et al., Trehalose preserves DDA/TDB liposomes and their adjuvant effect during freeze-drying. Biochim Biophys Acta, 2007. 1768 (9): p. 2120-2129.
46. Izutsu, K., S. Yoshioka, and T. Terao, Effect of mannitol crystallinity on the stabilization of enzymes during freeze-drying. Chem Pharm Bull (Tokyo), 1994. 42 (1): p. 5-8.
47. Kim, A. I., M. J. Akers, and S. L. Nail, The physical state of mannitol after freeze-drying: effects of mannitol concentration, freezing rate, and a noncrystallizing cosolute. J Pharm Sci, 1998. 87 (8): p. 931-5.
48. Kreilgaard, L., et al., Effects of additives on the stability of recombinant human factor XIII during freeze-drying and storage in the dried solid. Arch Biochem Biophys, 1998. 360 (1): p. 121-34.
49. Leal, M. L., et al., Study on thermostabilizers for trivalent oral poliomyelitis vaccine. Mem Inst Oswaldo Cruz, 1990. 85 (3): p. 329-38.
50. Liska, V., et al., Evaluation of a recombinant human gelatin as a substitute for a hydrolyzed porcine gelatin in a refrigerator-stable Oka/Merck live varicella vaccine. J Immune Based Ther Vaccines, 2007. 5: p. 4.
51. Melnick, J. L., Thermostability of poliovirus and measles vaccines. Dev Biol Stand, 1996. 87: p. 155-60.
52. Nagel, J., et al., Some experiments on freezedrying of inactivated poliomyelitis-vaccines. Arch Gesamte Virusforsch, 1963. 12: p. 718-20.
53. Ohtake, S., et al., Heat-stable measles vaccine produced by spray drying. Vaccine, 2010. 28 (5): p. 1275-84.
54. Sood, D. K., et al., Study on the stability of 17D-204 yellow fever vaccine before and after stabilization. Vaccine, 1993. 11 (11): p. 1124-8.
55. Ungar, J., et al., Preparation and properties of a freeze-dried B.C.G. vaccine of increased stability. Br Med J, 1962. 2 (5312): p. 1086-9.
56. Wang, W., Instability, stabilization, and formulation of liquid protein pharmaceuticals. Int J Pharm, 1999. 185 (2): p. 129-88.
57. Wright, D., P. W. Muggleton, and M. I. Griffiths, Evaluation of the stability of dried BCG vaccine. Tubercle, 1972. 53 (2): p. 92-9.
58. Izutsu, K., C. Yomota, and N. Aoyagi, Inhibition of mannitol crystallization in frozen solutions by sodium phosphates and citrates. Chem Pharm Bull (Tokyo), 2007. 55 (4): p. 565-70.
59. Shiomi, H., T. Urasawa, and S. Urasawa, Heat stability of the lyophilized Sabin poliovaccine. Jpn J Infect Dis, 2003. 56 (2): p. 70-2.
60. Burke, C. J., et al., The adsorption of proteins to pharmaceutical container surfaces. International Journal of Pharmaceutics, 1992. 86 (1): p. 89-93.
61. Kersten, G., T. Hazendonk, and C. Beuvery, Antigenic and immunogenic properties of inactivated polio vaccine made from Sabin strains. Vaccine, 1999. 17 (15-16): p. 2059-2066.
62. Doel, T. R., et al., The evaluation of a physical method for the quantification of inactivated poliovirus particles and its relationship to D-antigenicity and potency testing in rats. J Biol Stand, 1984. 12 (1): p. 93-9.
63. Ivanov, A. P. and E. M. Dragunsky, ELISA as a possible alternative to the neutralization test for evaluating the immune response to poliovirus vaccines. Expert Rev Vaccines, 2005. 4 (2): p. 167-72.
64. van Steenis, G., A. L. van Wezel, and V. M. Sekhuis, Potency testing of killed polio vaccine in rats. Dev Biol Stand, 1981. 47: p. 119-28.
65. Wood, D. J. and A. B. Heath, A WHO collaborative study of immunogenicity assays of inactivated poliovirus vaccines. Biologicals, 1995. 23 (4): p. 301-11.

ABBREVIATIONS

BCG—Bacillus Calmette-Guérin
DoE—Design of Experiments
DSC—Differential Scanning calorimetry
DU/D-Ag—D-Unit/D-antigenicity
ELISA—Enzyme-Linked ImmunoSorbent Assay
HES—Hydroxyethyl starch
HRP—Horseradish peroxidase
IgG—Immunoglobulin G
IPV—Inactivated Polio Vaccine
MAN—Mannitol
MS—Mass Spectrometry
MSG—Mono-Sodium Glutamate
OPV—Oral Polio Vaccine
PEP—Peptone
QC—Quality Control (department at RIVM)
RIVM—National Institute for Public Health and Environment
RMC—Residual Moisture Content
RP-HPLC—Reversed-Phase High-Performance Liquid Chromatography
sIPV—Sabin Inactivated Polio Vaccine (based on Sabin strains)
SOR—Sorbitol
SUC—Sucrose
$T_g$—Glass transition temperature
TREH—Trehalose
VAPP—Vaccine Associated Paralytic Poliomyelitis
VDPV—Vaccine Derived Poliovirus
WHO—World Health Organisation

The invention claimed is:
1. A method for producing a formulation of a biopharmaceutical agent, comprising drying a solution comprising:
   (a) a biopharmaceutical agent comprising poliovirus,
   (b) an amino acid selected from the group consisting of glutamate, arginine, histidine, glycine and mixtures thereof,
(c) a polyol comprising sorbitol and/or mannitol, and
(d) at least 0.2% (w/v) of a metal salt and water, wherein the metal salt is $Mg^{2+}$, $Ca^{2+}$, $Li^{+}$ or a mixture thereof.

2. The method according to claim 1, wherein the solution consists essentially of 1 pg-10 g per ml of the biopharmaceutical agent, 0.01-20% (w/v) of the amino acid, 0.5-20% (w/v) of the polyol, 0.2-10% (w/v) of the metal salt and water.

3. The method according to claim 1, wherein the glutamate is dissolved in the solution in the form of monosodium glutamate, and/or wherein the arginine is in the form of poly-L-arginine.

4. The method according to claim 3, wherein the solution consists essentially of 1 pg-10 g per ml of the biopharmaceutical agent, 5-20% (w/v) sorbitol, 5-20% (w/v) monosodium glutamate, 2-10% (w/v) of a magnesium salt, and optionally 5-20% (w/v) mannitol.

5. The method according to claim 1, wherein the solution comprises a pharmaceutically acceptable buffer and is buffered at a neutral pH.

6. The method according to claim 1, wherein the drying is by air drying, vacuum drying, spray drying or by lyophilization.

7. The method according to claim 1, wherein the poliovirus is one or more of poliovirus serotypes 1, 2 or 3.

8. The method according to claim 1, wherein the poliovirus is inactivated.

9. The method according to claim 1, wherein the formulation, upon reconstitution in a liquid, retains at least 50% of the activity of the biopharmaceutical agent present in the solution prior to drying.

10. The method according to claim 9, wherein the formulation comprises at least two different poliovirus serotypes, and wherein the difference in loss of activities for the different agents is less than 50%, whereby the retained activity of the agent with the most loss in activity is expressed as percent of the retained activity of the agent with the least loss, which is set at 100%.

11. The method according to claim 1, wherein the formulation upon reconstitution after storage for at least one week at 45° C., retains at least 50% of the activity of the biopharmaceutical agent present in the solution prior to drying.

12. The method according to claim 11, wherein the formulation comprises at least two different poliovirus serotypes, and wherein the difference in loss of activities for the different agents is less than 50%, whereby the retained activity of the agent with the most loss in activity is expressed as percent of the retained activity of the agent with the least loss, which is set at 100%.

13. The method according to claim 4, wherein the magnesium salt is $MgCl_2$ and/or $MgSO_4$.

14. A method for producing a formulation of a biopharmaceutical agent, comprising drying a solution comprising poliovirus, glutamate, sorbitol, and at least 0.2% (w/v) of $Mg^{2+}$ metal salt and water.

15. The method according to claim 14, wherein the drying is by lyophilisation.

16. The method according to claim 15, wherein the drying is by vacuum drying.

* * * * *